US009745273B2

(12) United States Patent
Døskeland et al.

(10) Patent No.: US 9,745,273 B2
(45) Date of Patent: Aug. 29, 2017

(54) PHENAZINE DERIVATIVES AS ANTI-NEOPLASTIC AGENTS AND ANTI-INFECTIVE AGENTS

(71) Applicants: Universitetet I Oslo, Oslo (NO); Bergen Teknologioverføring AS, Bergen (NO); Université Claude Bernard Lyon 1, Villeurbanne (FR)

(72) Inventors: Stein Ove Døskeland, Bergen (NO); Pål Rongved, Oslo (NO); Lars Herfindal, Bergen (NO); Marc Le Borgne, Saint Germain au Mont D'Or (FR); Elvar Örn Viktorsson, Oslo (NO); Ove Alexander Høgmoen Åstrand, Oslo (NO)

(73) Assignees: Universitetet I Oslo, Oslo (NO); Bergen Teknologioverføring AS, Bergen (NO); Université Claude Bernard Lyon 1, Velleurbanne (FR)

( * ) Notice: Subject to any disclaimer, the term of this patent is extended or adjusted under 35 U.S.C. 154(b) by 0 days.

(21) Appl. No.: 15/032,778

(22) PCT Filed: Nov. 3, 2014

(86) PCT No.: PCT/GB2014/053265
§ 371 (c)(1),
(2) Date: Apr. 28, 2016

(87) PCT Pub. No.: WO2015/063516
PCT Pub. Date: May 7, 2015

(65) Prior Publication Data

US 2016/0251320 A1 Sep. 1, 2016

(30) Foreign Application Priority Data

Nov. 1, 2013 (GB) .................................. 1319363.6

(51) Int. Cl.

| | |
|---|---|
| ***C07D 241/46*** | (2006.01) |
| ***C07D 403/12*** | (2006.01) |
| ***C07D 403/14*** | (2006.01) |
| ***C07D 241/52*** | (2006.01) |
| ***C07D 405/14*** | (2006.01) |
| ***A61K 47/48*** | (2006.01) |
| ***C07F 9/6509*** | (2006.01) |
| ***C07D 405/12*** | (2006.01) |
| ***C08G 73/02*** | (2006.01) |
| ***C08B 37/16*** | (2006.01) |
| ***A61K 31/498*** | (2006.01) |

(52) U.S. Cl.
CPC .......... *C07D 241/52* (2013.01); *A61K 31/498* (2013.01); *A61K 47/48969* (2013.01); *C07D 405/12* (2013.01); *C07D 405/14* (2013.01); *C07F 9/650994* (2013.01); *C08B 37/0012* (2013.01); *C08G 73/0273* (2013.01)

(58) Field of Classification Search
CPC ... C07D 241/46; C07D 403/12; C07D 403/14
USPC .......................................... 514/250; 544/347
See application file for complete search history.

(56) References Cited

U.S. PATENT DOCUMENTS 3,530,130 A 9/1970 Leimgruber et al.

FOREIGN PATENT DOCUMENTS

| | | |
|---|---|---|
| GB | 1285010 | 8/1972 |
| GB | 1285314 | 8/1972 |
| GB | 1325142 | 8/1973 |
| WO | 2008/089283 | 7/2008 |

OTHER PUBLICATIONS

Garcia et al., "Reduced in vivo lung metastais of a breast cancer cell line after treatment with Herceptin mAb conjugated to chemotherapeutic drugs," Oncogne, 2013, pp. 2527-2533, vol. 32.
Myhren et al., "Iodinin (1,6-Dihydroxyphenazine 5,10-Dioxide) from *Streptosporangium* sp. Induces Apoptosis Selectively in Myeloid Leukemia Cell Lines and Patient Cells," Marine Drugs, 2013, pp. 332-349, vol. 11.
International Searching Authority, International Search Report and Written Opinion mailed on May 8, 2015, issued in connection with International Patent Application No. PCT/GB2014/053265, filed on Nov. 3, 2014 17 pages.
GB Intellectual Property Office, Search Report issued mailed on May 21, 2014, issued in connection with Application No. GB1319363.6, 5 pages.

*Primary Examiner* — Brenda Coleman
(74) *Attorney, Agent, or Firm* — McDonnell Boehnen Hulbert & Berghoff LLP

(57) ABSTRACT

Novel phenazine derivatives, methods for their preparation and their medical use, in particular as anti-neoplastic agents and anti-infective agents, are provided. Novel methods for the preparation of iodinin and myxin are also provided.

17 Claims, 1 Drawing Sheet

| | 3% | 10% | avvik | |
|---|---|---|---|---|
| C4H9 | 0 | 5.7 | 0 | -2.2 |
| C6H13 | 0 | 2.0 | 0 | 1.0 |
| C8H17 | 0 | 1.0 | 0 | 1.0 |
| C4F9 | 0 | 2.5 | 0 | -0.5 |
| C6F13 | 0 | 1.1 | 0 | -0.4 |
Empty particles
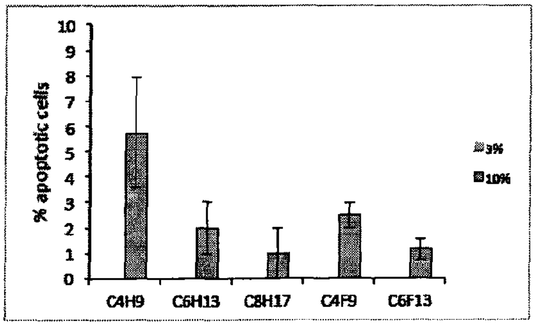
| | 3% | 10% | | |
|---|---|---|---|---|
| C4H9 | 75.4 | 95.5 | -12.7 | 1.9 |
| C6H13 | 16.4 | 91.0 | -0.1 | 6.0 |
| C8H17 | 42.5 | 95.1 | -10.8 | 2.4 |
| C4F9 | 7.9 | 66.7 | -5.9 | -3.0 |
| C6F13 | 79.9 | 89.6 | -1.9 | 3.0 |
Iodinin-filled particles
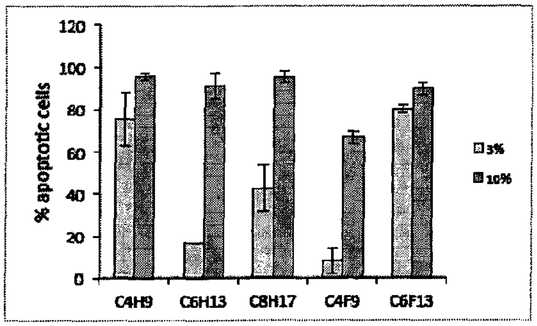
Apoptosis IPC-81 Leukaemia cells with empty or iodinin-filled cyclodextrins.

PHENAZINE DERIVATIVES AS ANTI-NEOPLASTIC AGENTS AND ANTI-INFECTIVE AGENTS

CROSS-REFERENCE

This application is a section 371 national phase application based PCT/GB2014/053265, filed Nov. 3, 2014, which claims priority to Great Britain Patent Appl. No. 1319363.6, filed Nov. 1, 2013, which are incorporated by reference in its entirety.

FIELD

The present invention relates to novel phenazine derivatives, methods for their preparation and their medical use, in particular as anti-neoplastic and anti-infective agents. In another aspect the invention relates to novel methods for the preparation of iodinin and myxin.

BACKGROUND

Acute myeloid leukemia (AML) is a hematopoietic stem cell disorder that causes excessive proliferation and rapid accumulation of myeloid precursor cells in the bone marrow. If left untreated, death occurs within weeks or months after diagnosis. AML is a heterogeneous disease. In the sub-group of promyelocytic leukemia (PML) with a specific chromosome translocation fusing the genes for the PML and RAR proteins, retinoic acid based differentiation therapy, in combination with an anthracycline drug, and sometimes the differentiation enhancer arsenic trioxide, has proven successful (P. Fenaux, C. Chastang, S. Chevret et al., *Blood* 94 (4), 1192 (1999). Improved therapy has also become available for patients with myelodysplastic syndrome, which eventually develops to aggressive AML. Their disease progression can be halted by drugs targeting DNA methylation and cytosine metabolism, namely 5-aza-cytidine (Vidaza) and 5-aza-2'-deoxycytidine (Dacogen). These chemically simple substances are, in spite of their limited effects on AML overall, presently the two most profitable AML drugs (Global Data, Pharma e-Track 2013). Sadly, for most AML patients, AML chemotherapy has not made significant progress in the last few years. It is still a 30 year old drug regime based on an anthracycline (Daunorubicin or Idarubicin) supplemented by arabinoside-C (ara-C) (A. Burnett, M. Wetzler, and B. Lowenberg, *J Clin Oncol* 29 (5), 487 (2011) and F. Ferrara and C. A. Schiffer, *Lancet* 381 (9865), 484 (2013)). Presently, complete remission is reached in 30-40% of AML patients less than 60 years old, and less than 10% in patients older than 70 years (Mehta 2010). However, relapse risk is in the range of 45-50% in older patients, making AML the leading cause of death due to leukemia with a 5-year relative survival below 20%. Intensive chemotherapy often is severe with lethal side-effects, such as lesions in hematopoietic tissue, particularly the bone marrow, as well as the intestine and the heart (Joel et al, A. Rohatiner, in *Leukemia*, edited by E. D. Henderson, T. A. Lister, and M. F. Greaves (Saunders, Philadelphia, 2002), pp. 394). There is thus a need for novel compounds that selectively target leukemia blasts, and leave normal tissues and cells largely unaffected. Drugs based on disease-related molecular alterations in AML cells have so far been disappointing. An example is patients whose AML cells constitutively express active Flt-3 tyrosine kinase, who benefit little from Flt-3 inhibitors. Thus, there is a major clinical need for new drugs in leukaemia therapy.

Iodinin (Scheme 1) has been known for almost a centennial, and is a member of the phenazine family. It is a planar nitrogen-containing heterocyclic compound produced by a variety of bacteria. Iodinin is an oxidized phenazine, namely 1,6-dihydroxyphenazine-5,10-dioxide, see Scheme 1.

Structure 1 Structures of iodinin, myxin, and tirapazamine

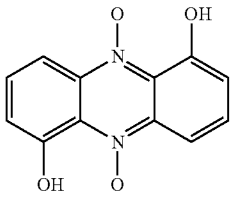

Iodinin

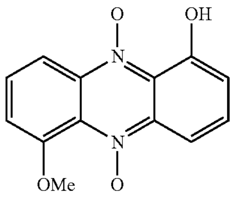

Myxin

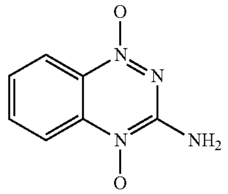

Tirapazamine

Iodinin can be obtained in different ways, the first and the most widespread is by bacterial production. The first iodinin-producing bacterium, a terrestrial bacteria, *Chromobacterium iodinum* was named owing to the purple, bronze-glinting pigment which covers its colonies on suitable solid media (McIlwain H, Biochem J 1943). This pigment, the iodinin, was found to inhibit the growth of certain other bacteria. Iodinin is also produced by *Pseudomonas phenazinium* (Byng G S et al, J. Gen. Microbiol. 1976; 97: 57-62), when grown on a variety of carbon sources, especially L-threonine. A second carbon growth dependant is the biosynthesis by *Brevibacterium iodinum* (Gerber N N et al, *Biochem* 1967; 6(9): 2701-2705). The highest yield of iodinin production occurred in experiments with resting cells in the presence of some three-, four-, or five-carbon amino acids. Tricarboxylic acid cycle compounds, especially succinic acid, also gave high yields. Another biosynthesis by *Arthrobacter paraffineus* KY 7134 (Suzuki T et al, Agr. Biol. Chem. 1971; 35(1): 92-98), on n-paraffin as the only source of carbon, produced two sorts of crystalline pigments in the culture medium, one yellow and one deep-red, corresponding respectively to 1,6-dihydroxyphenazine (iodinin intermediate) and 1,6-dihydroxyphenazine-5,10-di-N-oxide (iodinin). Microorganisms forming a novel group of Nocardiaceae were seen to produce slants with lustrous coppery needles on the mycelium and in the agar, characteristic of Iodinin crystals (Gerber N N., 1966; 5(12): 3824-3829). Another production of iodinin, as a culture metabolite, is also possible after growth of *Acidithiobacillus ferrooxidans* on elemental sulfur (Ceskova P et al. Folia Microbial. 2002; 47(1): 78-80).

The second process for obtaining iodinin is through fungal production. Iodinin was isolated from a soil sample, *Nocardiopsis dassonvillei* (*N. syringae, N. mutabilis* and *N. atra*), an alkalophilic actinomycete, strain OPC-15, that produced different phenazine antibiotics under different culture conditions, including Iodinin. (Tsujibo H et al. Agric. Biol. Chem. 1982; 52(2): 301-306). Other *Actinomycetes*, e.g. *microbispora amethystogenes* and *parva, streptosporangium album* and *amethystogenes*, realize extracellular production of characteristic iodinin violet crystal (pigment) in oat-meal agar medium (Tanabe I et al. J. Ferment. Bioeng. 1995; 79 (4): 384-386). An efficient method could be fungal metabolite screening, showing the production of many mycotoxins and fungal metabolites, possibly containing iodinin (Nielsen K F. Journal of Chromatography A 2003; 1002: 111-136).

Iodinin is chemically related to the compound tirapazamine (SR-4233) which is an experimental anticancer drug. Tirapazamine also has the N-oxide functionality (Scheme 1) and is activated to its toxic form preferentially in the hypoxic areas of solid tumors. Thus the combination of tirapazamine with conventional anticancer treatments is particularly effective. Tirapazamine has undergone phase III testing in patients with head and neck cancer and gynecological cancer, and similar trials have been undertaken for other solid tumor types (Denny, W A "Prospects for hypoxia-activated anticancer drugs" Current Medicinal Chemistry 4 (5): 395-9, 2004).

Iodinin is also found as bioactive metabolites from marine biological resources. As the bio prospecting for marine compounds is expanding, it has been discovered that some Marine *actinomycetes bacterium* and marine *Actinomadura* sp. are proven to be the best, offering a great biological diversity and therefore a great chemical diversity. Other microorganisms like *microbispora aerata, pseudomonas iodina*, and *streptomyces thioluteus* are capable of synthesizing 1,6-Phenazinediol-5-oxide, an intermediate of the Iodinin biosynthesis (Gerber N N et al. Biochem 1965; 4 (1): 176-180).

The biological properties of the phenazine class of natural products include antibiotic, antitumor, antimalaria, and antiparasitic activities. The physiological function leading to these activities can be inhibition/control of DNA, RNA, and protein synthesis as well as disruption of energy requiring membrane-associated metabolic processes. The planar, aromatic iodinin core has structural similarities to known intercalators, e.g. daunorubicin, and thus acts as a DNA intercalating agent, with a much lower cardiac toxicity. The interaction phenazine-DNA was shown by differences in the comparison between the UV/visible spectrum of a phenazine in the presence of GC and AT-rich double-stranded oligonucleotides, and the spectrum of pure phenazine. Although no binding to single-stranded DNA was observed, the binding with double-stranded DNA occurred with strong association constants, in the $10^{-4}$-$10^{-6}$ $M^{-1}$ range, comparable to those of ethidium bromide (Hollstein U et al. Biochem 1971; 10 (3): 497-504). The use of iodinin and myxin is only briefly reported in the prior art. One study reported low activity against a mouse sarcoma model (Endo et al, Tohoku University. Ser. C, Medicine 14 (3), 169 (1967). Iodinin has a number of biological effects. In U.S. Pat. No. 3,764,679 iodinin is claimed to have antihypertensive effects.

It was recently reported that iodinin, extracted for a bio prospecting screen of marine actinomycetes bacteria, had a pronounced effect on AML cells (Myhren et al, Marine drugs 11 (2), 332 (2013) and was found to be particularly potent against leukaemia cell lines and AML-patient blasts. It was less toxic than DNR (at comparable anti-AML activity) towards peripheral blood leukocytes (PBL), rat cardiomyoblasts and blood platelets. Even direct infusion of a supra-saturated solution of iodinin into the gut of the mouse through a tube failed to cause any intestinal symptoms or histologically detectable alteration of the intestinal mucosa, like mucositis, which is common after anthracycline treatment. Thus, iodinin is an attractive potential drug for treatment of AML.

However, synthesis of phenazines and its derivatives are sparsely described in the prior art. One example is the Wohl-Aue reaction (Patcher I J et al. J. Am. Chem. Soc. 1951; 73 (10), 4958-4961), an organic reaction between an aromatic nitro compound and an aniline to form a phenazine in the presence of an alkali base. This method of synthesis was the first to have been used to synthesize the phenazine core. It has nonetheless a major issue; the reaction's yield is below 20%. Synthesis of phenazine derivatives by Cu-catalyzed homocoupling of 2-halogenoanilines in water has been proposed (Yu L et al. J Organomet Chem 2012; 705: 75-78)—see Scheme 2 below:

Scheme 2 The Cu-catalysed homocoupling procedure

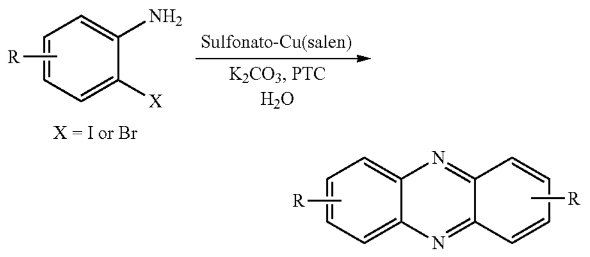

In spite of their promising biological effects, iodinin/myxin have several major disadvantages: a) they are practically insoluble in water, hindering in vivo testing in mammals; b) they can only be obtained by bio prospecting, which is laborious and expensive yielding only milligram quantities of the substance at a high cost and the process is time-consuming; no synthetic preparation process is known in the prior art for these two compounds; and c) they have a non-selective bio distribution in vivo and lack the chemical functionality required to attach functional groups for regulating their bio distribution. In the prior art, these problems are not properly addressed. In US 2009/042894 a biotechnological procedure is suggested to produce iodinin. In DE 2016467, DE 2115660, U.S. Pat. No. 3,929,790, U.S. Pat. No. 3,937,707, WO 2008/089283, and in Alonso et al, Chem. Comm. 2004, 41, 412-413, methods to alkylate iodinin or myxin via their alkali salts is described. However, the functional groups introduced were alkyl groups, rendering the derivatives less water soluble than the parent compounds. No discussion of improvement in water solubility was described.

SUMMARY

The present invention provides novel phenazine derivatives, methods for their preparation and their medical use, in particular as anti-neoplastic agents and anti-infective agents. The invention further relates to novel methods for the preparation of iodinin and myxin.

In one embodiment, a compound of formula I or a physiologically acceptable salt thereof is provided:

(I)

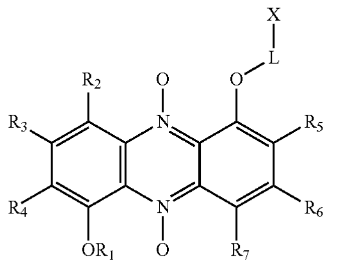

wherein $R_1$ is selected from:

hydrogen, an optionally substituted $C_{1-6}$ alkyl group (preferably $C_{1-3}$ alkyl, e.g. methyl), an optionally substituted $C_{3-7}$ cycloalkyl group (preferably $C_{3-5}$ cycloalkyl), an optionally substituted aryl group (preferably one containing from 6-20 carbon atoms, more preferably one containing either 6 or 10 carbon atoms, e.g. phenyl), and a group -L-X in which L and X are as defined herein;

$R_2$ to $R_7$ are each independently selected from:

hydrogen, an optionally substituted $C_{1-6}$ alkyl group (preferably $C_{1-3}$ alkyl, e.g. methyl), an optionally substituted $C_{2-6}$ alkenyl group (preferably $C_{2-4}$ alkenyl), an optionally substituted $C_{3-7}$ cycloalkyl group (preferably $C_{3-5}$ cycloalkyl), and an optionally substituted aryl group (preferably one containing from 6-20 carbon atoms, more preferably one containing either 6 or 10 carbon atoms, e.g. phenyl);

L is either a direct bond or a linker, preferably a linker cleavable in vivo by one or more biological enzymes (e.g. esterases, amidases and/or oxidative enzymes) or by a hydrolytic reaction;

X is a functional group, preferably a hydrophilic group (the term "hydrophilic" means that this portion of the molecule has a tendency to interact with or be dissolved by water or other polar solvents and/or substances), a group capable of polymerization (preferably lactic acid, lactide or a vinylic group, e.g. acrylic acid), or a group capable of coupling to a biological molecule (e.g. a peptide or a protein); or is a biocompatible polymer (e.g. polylysine, dextran, polylactic acid, chitosan or alginate, preferably polylysine); and wherein, when $R_1$ is a group -L-X, each L and X may be the same or different.

In another embodiment, a compound is provided which is a polymer having the formula:

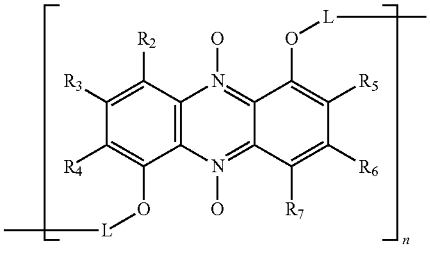

wherein n is an integer of at least 2;

each of $R_2$ to $R_7$ are as defined in any one of claims 1 to 5; and

L is as defined in any one of claims 1, 6, 7 and 8, for example wherein L is selected from the following structures:

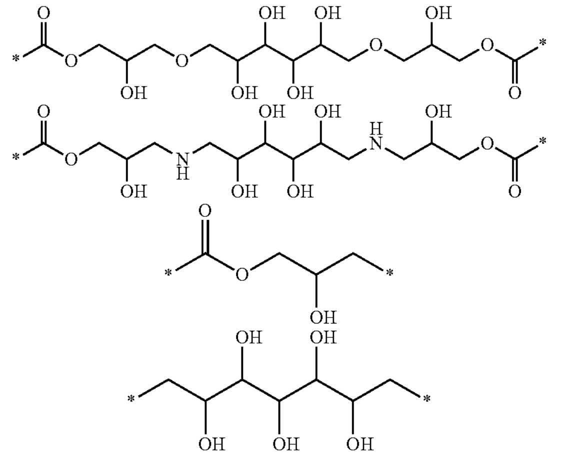

where each * denotes the point of attachment of the linker, L, to adjacent groups within the molecule.

In another embodiment, a pharmaceutical composition comprising the aforementioned compounds or a physiologically acceptable salt thereof, together with one or more pharmaceutically acceptable carriers or excipients is provided.

DESCRIPTION OF THE DRAWINGS

The FIGURE illustrates the results of an in vitro biological evaluation of 3% or 10% formulations of either empty or iodinin-filled cyclodextrin nanoparticles in IPC-81 leukaemia cells. Apoptosis was assessed by microscopic evaluation.

DETAILED DESCRIPTION

GB 1285314 A, GB 1325142 A and GB 1285010 A (Hoffman La Roche) and WO 2008/089283 (JJ Pharma Inc.) describe derivatives of iodinin for treating bacterial infections. However, as evident from the general formulas and the experimental procedures in these documents the resulting compounds are not water-soluble. These therefore do not solve the basic solubility problem, for example where there may be a need to prepare solutions of the compounds for injection. Further, these documents use as the starting material iodinin from natural sources. As such, these methods would be a tedious procedure for large scale preparation of material for drug development.

It has now surprisingly been found that all these obstacles can be resolved. First, in the prior art, no total synthesis of iodinin is described, in spite of its attractive medical properties. In U.S. Pat. No. 3,432,505 and U.S. Pat. No. 3,700,679 methods for preparing alkylated derivatives of iodinin and myxin are described. However, the products are more lipophilic than the parent compounds, and the starting material is, in most cases, iodinin isolated from natural sources (this is a tedious and expensive process). Reported methods are also hampered by low yields (Chowdhury et al, Chem. Res. Toxicol. 2012, 25, 197-206) or formation of side products (Tracy et al, J. *Org*. Chem. 1984, 49, 5116-5124, Alonso et al, Org. Biomol Chem, 2005, 3, 2832-2841).

The present invention describes the first total synthesis of iodinin, myxin and their derivatives providing the compounds in high yield, notably in a yield acceptable for an industrial process. Iodinin has now been prepared in at least 51% total yield using standard and scalable methods from the cheap and commercially available starting material 2-bromo-3-methoxyaniline. Using this process, myxin can also be produced in a total yield of at least 26%. This is a novel, general and convenient synthesis of iodinin, myxin and their derivatives from commercially available building blocks, suitable for a convenient large-scale production process (see Schemes 3a and 3b).

Scheme 3a A novel general process for iodinin, myxin and derivatives

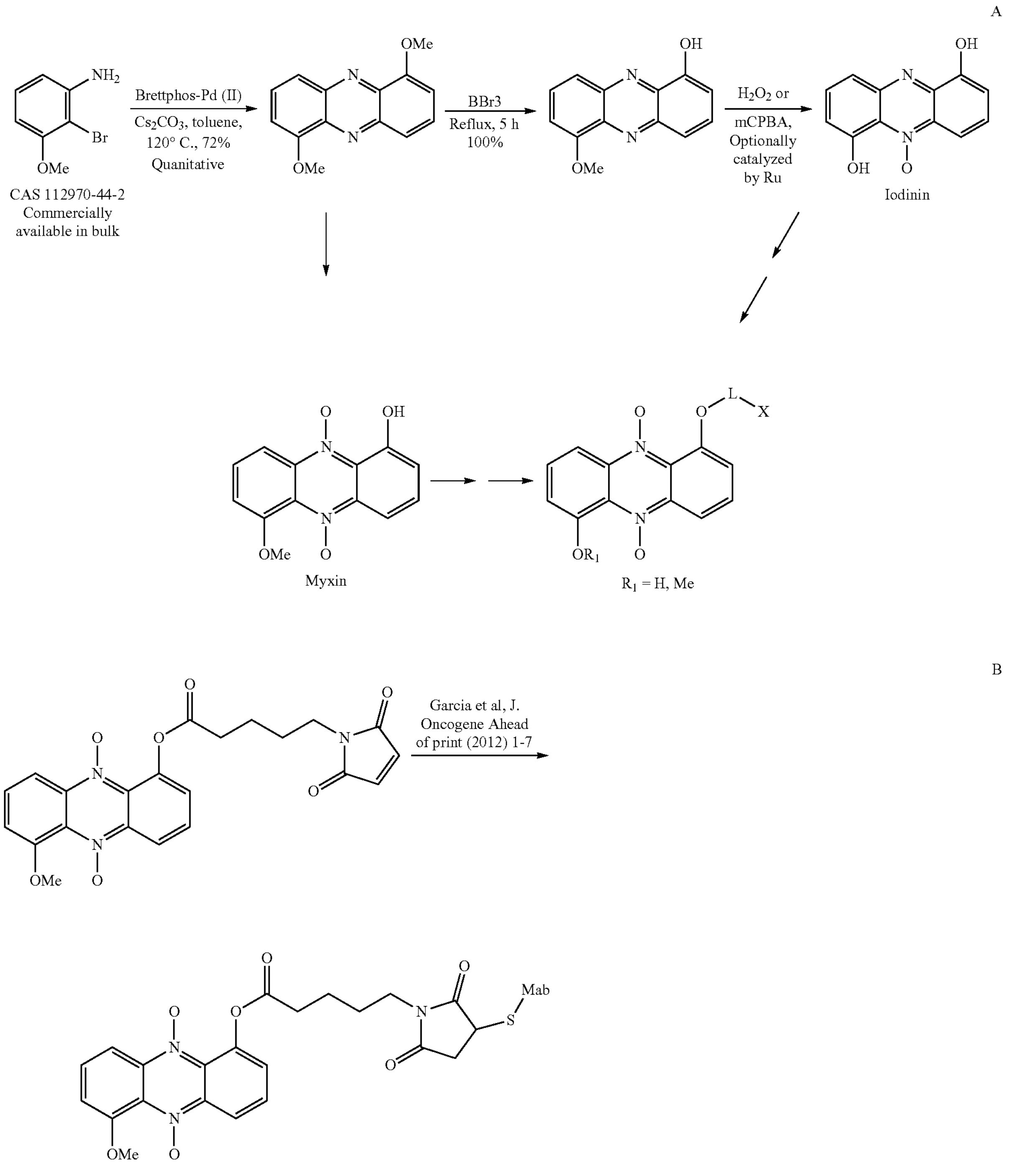

CAS 112970-44-2
Commercially available in bulk

Iodinin

Myxin $R_1$ = H, Me

Scheme 3b A novel general process for iodinin, myxin and derivatives

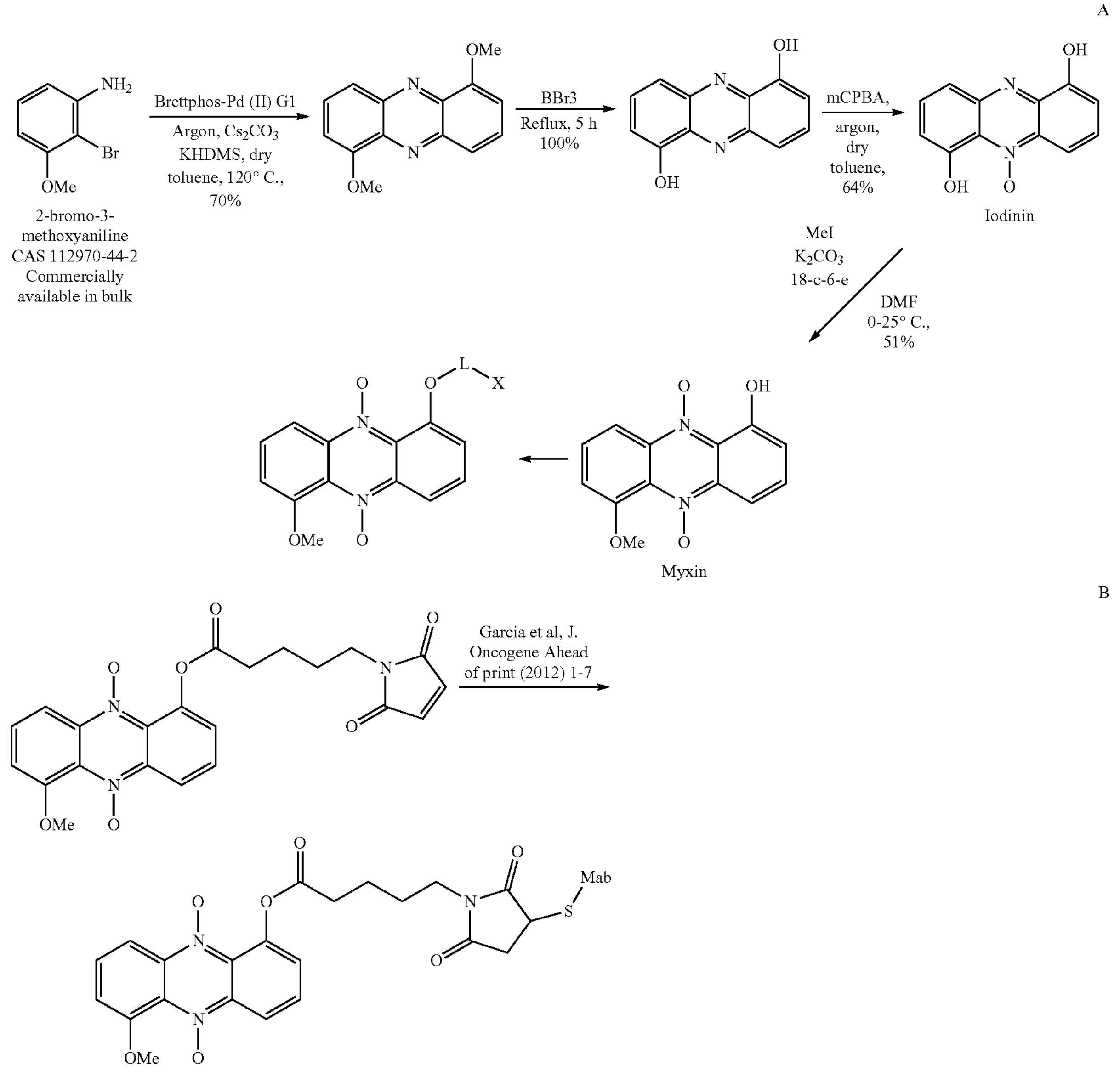

2-bromo-3-methoxyaniline
CAS 112970-44-2
Commercially available in bulk

Iodinin

Myxin

Based on this chemistry, iodinin and myxin can conveniently be prepared. Yet another preferred aspect of this method is that myxin or iodinin can be used as a starting material for preparation of a derivative for functionalization with peptides, proteins or other desired vectors to achieve enhanced specificity for the desired tissue. In Scheme 3a, it is depicted how a construct with a functionality —O-L-X can be prepared using state of the art chemistry, where L is any linker suitable for the purpose, e.g. an alkyl chain. X is a functional group that is active or which can be activated for covalent attachment to e.g. a peptide, a monoclonal antibody (mab, Scheme 3b) or another functional group capable of providing uptake or affinity for the tissue of interest. Where X is a functional group, this may be a hydrophilic group (the term "hydrophilic" means that this portion of the molecule has a tendency to interact with or be dissolved by water or other polar solvents and/or substances). Non-limiting examples of hydrophilic groups that may be comprised by X include phosphonic acid, sulphonic acid, and carboxylic acid groups or salts thereof, (poly)hydroxyl-alkyl- or (poly)hydroxyl-alkylamino groups, polyethyleneoxide groups, carbohydrate groups like glucuronic acid, amino sugars like 2-deoxy-2-amino glucose or amino acid derivatives.

Further, based on the same chemistry, it has been found that this process can be used to produce (i) water soluble derivatives or formulations of iodinin/myxin enabling use of the parent compounds in in vivo studies in mammals, (ii) polymerized biodegradable iodinin, that will enable polymer-based nano-formulations of the drug, (iii) linker technology is also provided, that will enable linkage of both iodinin and myxin to peptides and proteins, e.g. monoclonal antibodies (mab), providing drug delivery to a site of interest with better therapeutic index, (iv) unsymmetrical phenazine analogues for structure activity studies (SAR), and (v) novel nanonization methods which can be used to form nanoparticles and colloids from iodinin/myxin.

The biological absorption of iodinin, myxin or derivatives thereof can be enhanced by different nanonization strategies.

The compounds may be included in nanoparticles made by polymers like poly-lactic-co-glycolic acid (PLGA) using well established methods in prior art, e.g. in Kumar et al, "Nano medicine in Drug Delivery", CRC Press, Taylor & Francis Group, New York, 2013, and all references herein. Another state-of-art method is emulsion-evaporation, e.g. by dissolving the compound in e.g. chloroform. Preferably, the encapsulation efficiency should be above 10% with this method.

These technologies enable animal studies and research on improved derivatives and formulations with higher selectivity and therapeutic index. Another advantage with these drug delivery systems is that they allow for targeted therapy. One can modify the surface of the nano carriers to target specific organs, like calcified tissue, neovasculature and others, or cancer cells. For AML, the folate receptor 2 has been evaluated as a drug carrier target, but also receptors like CD11 or CD33 can be targeted by antibodies (mab) or antibody fragments.

One aspect of the formulations referred to in (i) relates to the water-soluble prodrugs and polymers as described below. One attractive example of prodrugs of iodinin/myxin is derivatization to phosphates or bisphosphonates that have specificity for bone marrow, an especially valuable technology for leukaemia drugs. The chemistry of the prodrug technique is described in the prior art, e.g. in WO 2012/042024, EP 2289558, WO 2012/113571 and in Journal of Drug Targeting, 1996, Vol. 4, pp. 117-123, but the combination with iodinin/myxin is novel.

Preferred structures are given in Scheme 4, where L is a linker and A is an alkyl or heteroalkyl group.

Scheme 4 Iodinin and myxin prodrugs with higher water-solubility

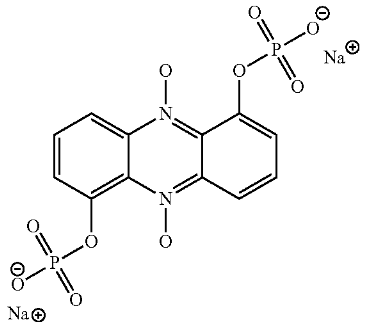

-continued

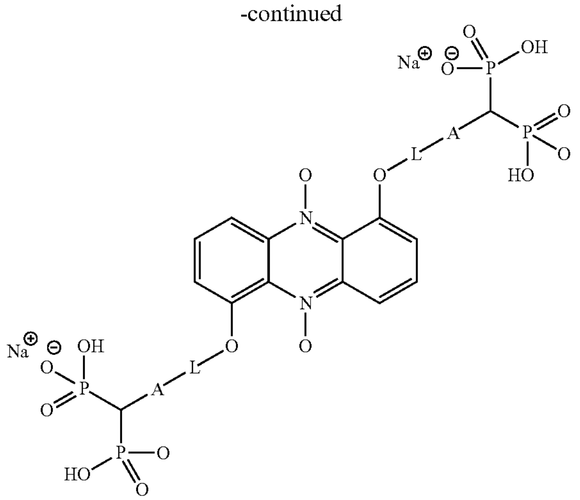

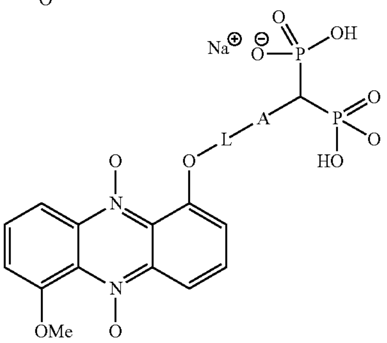

Other novel water-soluble derivatives of iodinin and myxin can be prepared using state of the art chemistry, given as non-limiting examples in Scheme 5. Both the monomers and polymer comprise ester, acetal and carbonate bonds that are degradable by in vivo proteases such as esterases. A preferred method is to produce polymers that consist of iodinin, e.g. with the polymeric form shown in Scheme 5a. These can be precipitated as nano colloids alone, or together with functionalized polymers like PEG-PLG+A to obtain surface modifications.

Scheme 5a: Iodinin polymer based on tartaric acid polymerization

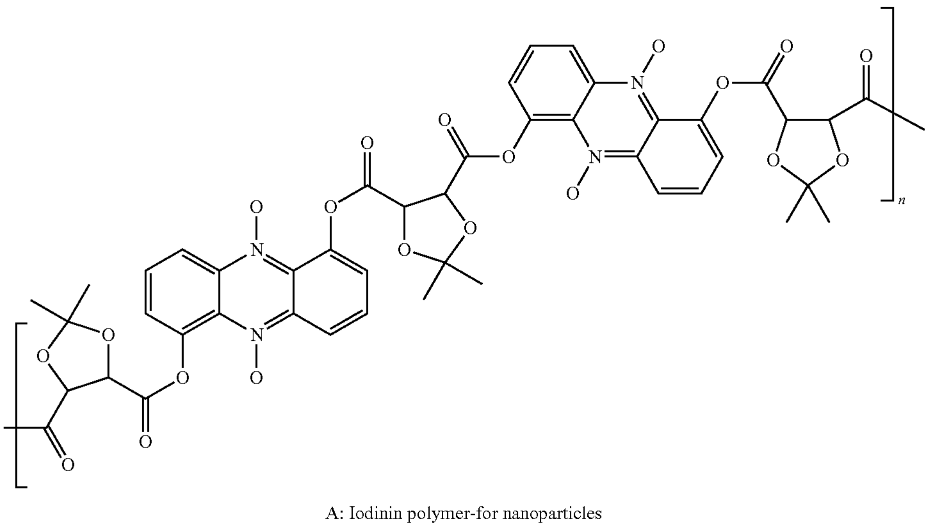

A: Iodinin polymer-for nanoparticles

Scheme 5b: Water-soluble derivatives of iodin based on alkylation or acylation with biocompatible side chains

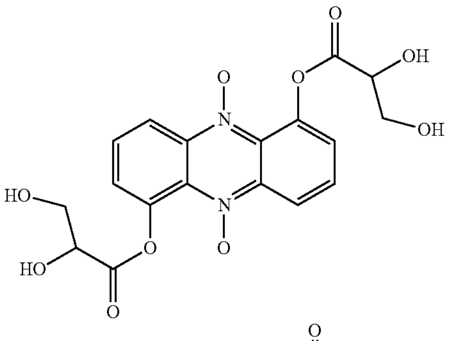

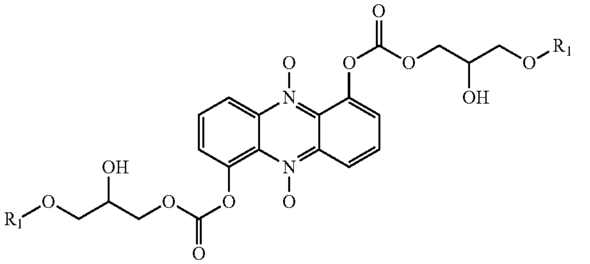

B: Water soluble monomers of iodin. $R_1$ = H (water-soluble, biodegradable) $R_1$ = Iodin derivative (Iodin biodgradable polymer)

Iodinin is bifunctional, so in principle any type of polymerization is possible using the proper linker. Suitable methods of polymerization would be identifiable by those skilled in the art and include, for example, block-copolymerization with biocompatible polymers such as polylactic acid, condensation polymerisation using a bifunctional reagent reactive with the phenoxy anions on iodinin, or radical polymerization.

Myxin is monofunctional, but can be derivatized on the free OH group with anything that polymerizes, for example acrylic acid, vinylic groups or bifunctional side chains that may be activated for polymerisation. Lactic acid polymerization techniques may also be employed.

Myxin may also conveniently be attached covalently with a biodegradable bond to a biocompatible polymer for drug delivery, e.g. dextran, polylysine, poly(lactic acid), chitosan or alginate. Polylysine is cationic and may enhance intracellular uptake of the drug.

Another favourable aspect for providing formulations of iodinin/myxin for biological studies is the use of drug delivery tools to enhance drug efficacy. The use of nano-carriers are particularly interesting to galenic pharmacy, since these address several of the problems seen with conventional drug administration without changing the chemical structure of the active compound. Such problems can include poor solubility of the drug, rapid excretion by kidneys or metabolism in the liver, or toxic side effects on non-diseased organs or tissues. Nano-colloids are small (approx. 30-150 nm) colloidal drug carriers that are used to modify the distribution of the associated compound. If they are carefully designed with respect to the target and route of administration, they may be used to overcome the delivery problems posed by several promising drug classes such as peptides, proteins and other compounds with short biological half-life. Particularly interesting is the possibility to label nanoparticles with ligands that bind directly to the target. Many nano-carriers, such as liposomes and polymeric nano-colloids can be made from biodegradable constituents that are approved for human use. One method for achieving this is to use a block-copolymer with iodinin and tartaric acid acetonide as the components as illustrated in Scheme 6.

Polymers of iodinin may be achieved using polymerization reactions as described in the literature related to epoxy resins (see Schemes 6 and 7). Suitable polymerization reactions include those described in Liang (US 2009/0181165), in Imai et al, Macromolecules 2003, 36, 6359-6363, in De et al, ACS Sustainable Chem. Eng. 2014, 2, 445-453, in Takano et al, J. Am. Chem. Soc. 1991, 113, 2786-2787, in Thio et al, J. POLYM. SCI. PART B: POLYM. PHYS.: VOL. 47 (2009), and in Otvos et al, Tetrahedron Letters No. 29, pp 2477-2480, 1975. The reagents used in Schemes 6 and 7 to make polymers of iodinin are all described in the literature or are commercially available.

Scheme 6 Iodin polymer based polymerization of bis eopxy-derivatives of iodinin
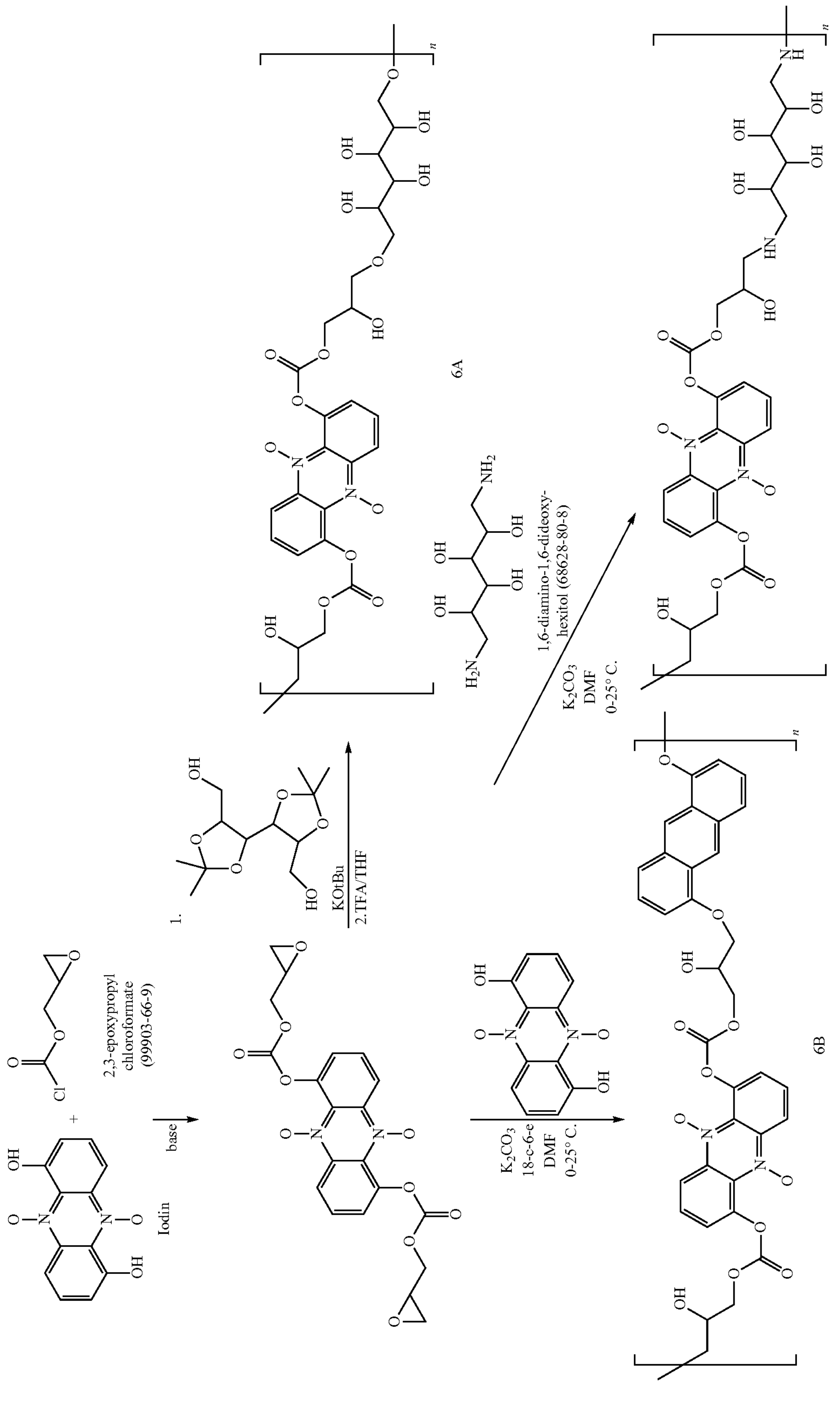

Scheme 7 Iodinin polymer based on bis-epoxy polymerization with iodinin and 1,4-di(oxiran-2-yl)butane-1,2,3,4-tetraol

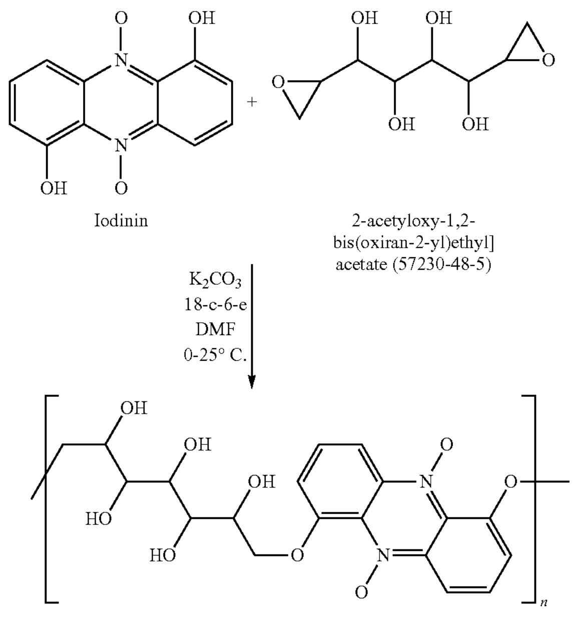

Iodinin is poorly soluble in biocompatible solvents, but is soluble in organic solvents such as toluene and chloroform. However, production of nano-carriers by emulsion-evaporation merit that the compound to be encapsulated must be dissolved in an organic solvent that is immiscible with water. The present invention enables the production of iodinin-encapsulated nanocarriers—iodinin and a biodegradable polymer can be dissolved in chloroform and mixed with water to make a nano-suspension, and organic solvent evaporated to co-precipitate the polymer with iodinin. To improve the nanonization of iodinin, a polymer can be precipitated to produce nanoparticles. The advantage of incorporating iodinin itself into a biodegradable polymer is that the drug load in the formulation may be higher. The particles may be coated with monoclonal antibodies, e.g. CD11 or CD33 against AML.

Another favourable aspect for providing iodinin/myxin which is easier to disperse in water is the use of state of the art cyclodextrins or especially derivatized cyclodextrins. New fluorinated or alkylated amphiphilic α-cyclodextrins (α-CD) have been designed to form nanoparticles with iodinin. The introduction of alkylated chains on the primary side leads these amphiphilic molecules to auto-assemble in aqueous media, increasing their stability and their ability to carry drugs, therefore increasing the bioavailability of active compounds. Alkylated cyclodextrin analogues were synthesized as reference compounds in order to determine the effect of the fluoro-alkylated chains (Perret F et al. Eur J Pharm Biopharm 2013; 83: 25-32).

The present invention comprises a novel method for preparation of iodinin and myxin and their derivatives, physiologically acceptable salts thereof or nanoparticle dispersions. The versatility of the method can be illustrated by Scheme 8, showing coupling of identical or two different building blocks to form the phenazine core. The method used for the coupling may be, but is not limited to, Pd-catalyzed Buchwald-Hartwig amination or Cu-salen catalyzed coupling (Yu et al, Journal of Organometallic Chemistry 705 (2012) 75-78). Thus the method may, in addition to preparing iodinin and myxin, be used to synthesize any variant of substituted iodinin and myxin. Thus the method may be used to prepare a library of compounds for SAR studies for identification of lead candidates in biological studies.

Scheme 8

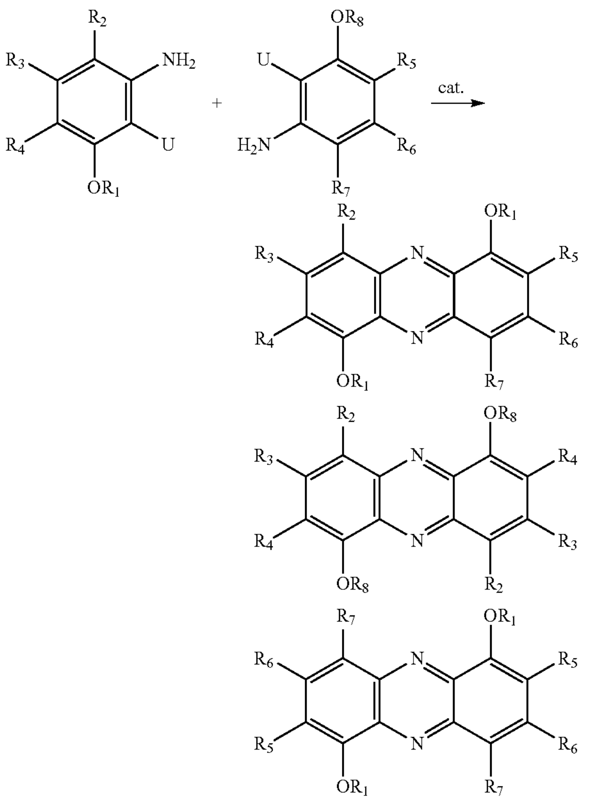

U is a leaving group, $R_1$-$R_8$ may independently be H, lower alkyl, alkoxy, alkylamino, halogen or any other group that provides diversity in a library of compounds for screening for optimized biological activity Also provided herein is a pharmaceutical composition comprising a compound according to the invention together with at least one pharmaceutically acceptable carrier or excipient.

Compositions comprising the compounds are preferably formulated prior to administration. The active ingredients in such compositions may comprise from 0.05% to 99% by weight of the formulation. Appropriate dosages may depend on the modulator to be used, precise condition to be treated, age and weight of the patient etc. and may be routinely determined by the skilled practitioner according to principles well known in the art. By way of example, representative dosages may include 1 to 200 or 1-100 mg/kg, e.g. 5 to 70, 5-50, or 10 to 70 or 10 to 50 mg/kg.

By "pharmaceutically acceptable" is meant that the ingredients must be compatible with other ingredients of the composition as well as physiologically acceptable to the recipient. Pharmaceutical compositions according to the present invention may be formulated according to techniques and procedures well known in the art and widely described in the literature and may comprise any of the known carriers, diluents or excipients. Other ingredients may of course also be included, according to techniques well known in the art e.g. stabilisers, preservatives, etc.

The formulations may be in the form of sterile aqueous solutions and/or suspensions of the pharmaceutically active ingredients, aerosols, ointments and the like. Especially preferred in the present invention are the formulations in a sustained release form e.g. microparticles, nanoparticles, emulsions, nanosuspensions, lipid particles or oils.

The suspensions in the form of nanoparticles comprising micelles or liposomes may be stabilised by one or more surface active agents, e.g. triglycerides, soaps and other carboxylates, anionic surfactants, proteins, sulfates sulfonates, ethoxylated alcohols and alkylphenols, fatty acid esters, nitrogenated nonionic surfactants, linear alkylamines, alkyl-ammoniums, nitrogenated surfactants with a second hydrophile, amphoteric surfactants, silicon surfactants, fluorinated surfactants, polymeric surfactants or surfactant polymers or association polymers.

The administration may be by any suitable method known in the medicinal arts, including oral, parenteral, topical, or subcutaneous administration or by inhalation. The compounds or formulations comprising the compounds may be may contain any of a number of adjuvants, such as buffers, preservatives, dispersing agents, agents that promote rapid onset of action or prolonged duration of action. Compositions/formulations suitable for oral administration may be in sterile purified stock powder form, preferably covered by an envelope or envelopes which may contain any of a number or adjuvants such as buffers, preservative agents, or agents that promote prolonged or rapid release. Compositions/formulations for use in the present invention suitable for local or topical administration may comprise the compound mixed with known suitable ingredients such as paraffin, vaseline, cetanol, glycerol and its like, to form suitable ointments or creams.

The invention will now be further described with reference to the following non-limiting examples.

EXAMPLE 1

Synthesis of Iodinin (4)

Scheme 9 Reaction scheme for the synthesis of iodinin (4) and myxin (6)

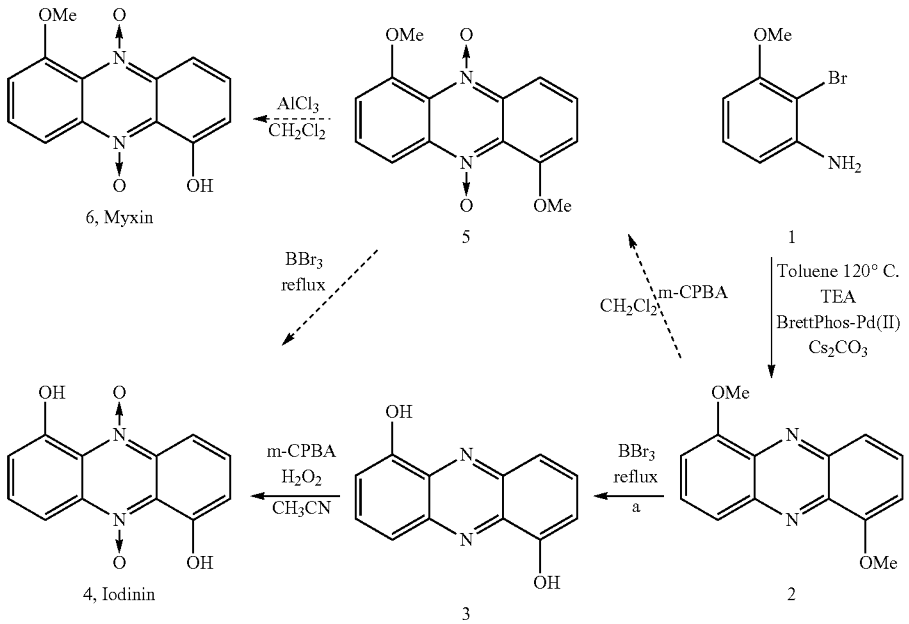

6, Myxin

5

1

4, Iodinin

3

2 administered in a single dose to be taken at regular intervals e.g. once or twice a day, once every 48 hours or once every 72 hours. Sustained formulations may be given at longer intervals e.g. 1 to 2 times a month or every three months. The precise dosage of the active compounds to be administered, the number of daily or monthly doses and the length of the course of treatment will depend on a number of factors, including the age of the patient and their weight.

The compositions may be formulated according to techniques and procedures well known in the literature and may comprise any of the known carriers, diluents or excipients. For example the compositions/formulations which can be used in the present invention which are suitable for parenteral administration conveniently may comprise sterile aqueous solutions and/or suspensions of pharmaceutically active ingredients preferably made isotonic with the blood of the recipient generally using sodium chloride, glycerin, glucose, mannitol, sorbitol and the like. In addition, the composition The process was carried out using a modified Buchwald-Hartwig reaction to give excellent yields (quantitative) of the 1,6-dimethoxy-phenazin. Demethylation of 2 by the Alonso-method (Alonso M A et al. Org. Biomol. Chem. 2005; 3: 2832-2841) by the Alonso-method (Alonso M A et al. Org. Biomol. Chem. 2005; 3: 2832-2841) using $BBr_3$ gave the 1,6-dihydroxy-phenazine in excellent yields (91%), that could be oxidized using m-CPBA to give iodinin (4).

a) Synthesis of 1,6-dimethoxyphenazine (2)

To a solution of 2-bromo-3-methoxyaniline (1) (1 eq) in toluene (0.1 M) was added BrettPhos-Pd(II) (0.05 eq), TEA (0.05) and $Cs_2CO_4$ (2 eq) at room temperature. The reaction mixture was allowed to stir and warm up to 120° C. for 4-24h. Once the reaction appeared to be completed by consumption of the bromide by TLC analysis (EtOAc/hexane=1:1), the mixture was allowed to cool to room temperature, diluted with $CHCl_3$, and filtered through celite. The solution was concentrated, loaded on silica gel, and purified by flash chromatography (hexane/EtOAc 5:1 to hexane/EtOAc 1:1) to give 2 as a yellow solid.

$^1$H NMR (300 MHz, $CDCl_3$) δ 7.97 (dd, J=8.9, 1.1 Hz, 1H), 7.71 (dd, J=8.9, 7.6 Hz, 1H), 7.06 (dd, J=7.7, 1.1 Hz, 1H), 4.15 (s, 3H). $^{13}$C NMR (101 MHz, $CDCl_3$) δ 155.06 (s), 143.15 (s), 137.03 (s), 130.23 (s), 122.19 (s), 106.99 (s), 56.60 (s).

c) Synthesis of 1,6-dimethoxyphenazine-N5,N10-dioxide (5)

To a solution of dichloromethane (10.5 mL) was added 2 (50 mg) and m-CPBA (416 mg, Aldrich, 77% max). The mixture was stirred for 2 h. Removal of solvent by rotary evaporation, followed by column chromatography on silica gel eluted with 100% ethyl acetate.

d) Synthesis of 1,6-dihydroxyphenazine (3)

Boron tribromide (1.52 ml, 16.1 mmol) was added to 4 (100 mg, 416.1 mmol) under nitrogen. The mixture was refluxed for 5 h, then cooled to room temperature, poured onto ice (20 g) and left overnight. The pH of the mixture was adjusted to 7 using NaOH. The yellow precipitate was filtered off, washed with water and dried to give 3 as a yellow solid.

e) Synthesis of 1,6-dihydroxyphenazine-N5,N10-dioxide (4, Iodinin)

To a solution of 3 (35 mg) in acetonitrile (8 mL) was added m-CPBA (400.3 mg, Aldrich, 77% max) and $H_2O_2$ (0.03 mL). The mixture was allowed to stir and warm up to 80° C. for 3 h. The reaction was monitored by TLC analysis ($CH_2Cl_2$/MeOH=9:1). Removal of solvent by rotary evaporation, followed by column chromatography on silica gel ($CH_2Cl_2$/MeOH=9:1 and $CH_2Cl_2$/MeOH 1%).

EXAMPLE 2

Synthesis of Cyclodextrin Derivatives

Synthesis of the α-cyclodextrins used in the present invention could be initiated using the introduction of the perfluoroalkyl chains (Bertino Ghera B et al. New J. Chem. 2007; 31: 1899-1906). From this, α-cyclodextrin nanoparticles with iodinin could be prepared. It has been reported that the highly loaded method was the most efficient for encapsulating hydrophobic compounds inside amphiphilic cylcodextrin based nanoparticles. Since iodinin is hydrophobic, we chose this method for its encapsulation.

a) Synthesis of per-(6-O-methylsulfonyl-2,3-di-O-methyl)-α-cyclodextrin (8)

To a solution of per-(2,3-di-O-methyl)-α-cyclodextrin (7) (40 mg, 35 μmol) in anhydrous pyridine (5 mL) was added at −10° C. methanesulfonyl chloride (100 μL, 1.29 mmol, 36 eq, 6 eq/OH). The mixture was stirred at 5° C. for 15 hours. The reaction was monitored by TLC ($Et_2O$/MeOH: 9/1) and was stopped by addition of saturated $NaHCO_3$ solution (10 mL). The aqueous phase was extracted with $CH_2Cl_2$. The organic phases were combined, dried over $Na_2SO_4$, and evaporated under vacuum. The pyridine was removed by several co-evaporation with toluene to give 8 as a brown solid.

b) General Procedure for the Synthesis of perfluoroalkylpropanethio- and alkylthio(2,3-di-O-methyl)-α-cyclodextrin (9, a-e)

A solution of isothiouronium iodide perfluoroalkylpropane (12 eq, 2 eq/OMs) and cesium carbonate (18 eq, 3 eq/OMs) in anhydrous DMF was stirred for two hours at room temperature. A solution of 8 (1 eq) in anhydrous DMF was then added dropwise over a period of 1 hour. The mixture was stirred for 3 days at 60° C. After cooling, salts were precipitated in acetone. The precipitate was then filtered and the filtrate evaporated under vacuum.

Scheme 10 Synthesis of 2,3-di-O-methyl-6-substituted-α-cyclodextrins

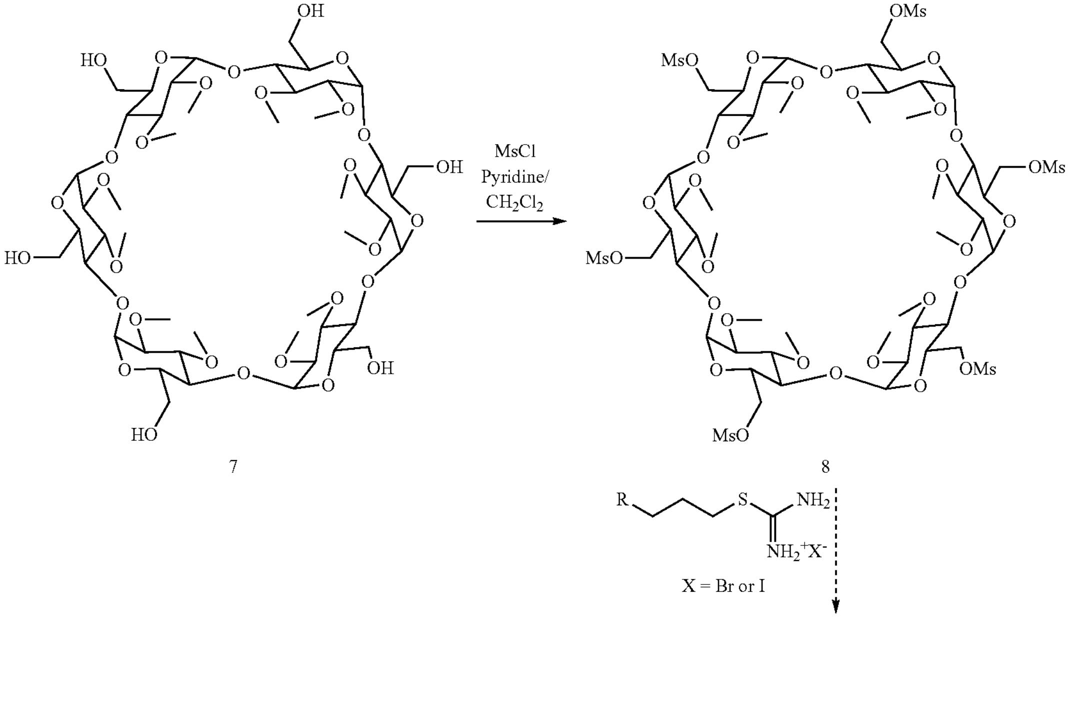

7 8

-continued

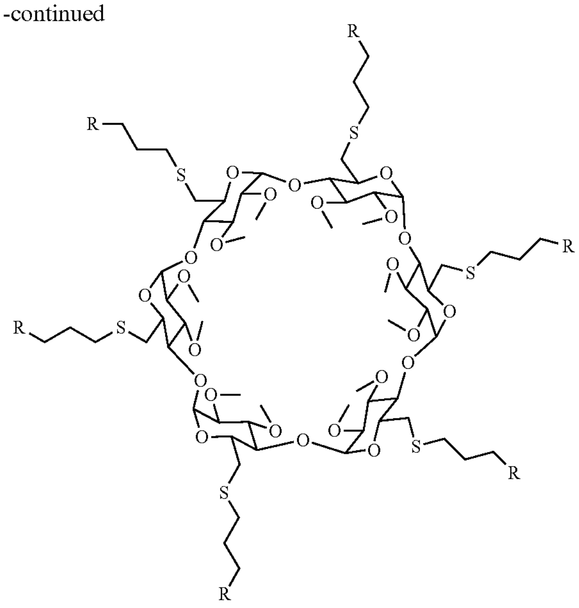

9 a-e
a: R = $C_4H_9$
b: R = $C_4F_9$
c: R = $C_6H_{13}$
d: R = $C_6F_{13}$
e: R = $C_8H_{17}$

EXAMPLE 3

Preparation and In Vitro Biological Testing of Cyclodextrin Nanoparticles a) Preparation of Nanoparticles by the Highly Loaded Method (Inert Atmosphere Unnecessary)

The iodinin loaded nanoparticles based on α-CD were prepared by the nanoprecipitation technique, using a $0.8 \cdot 10^{-4}$ M solution of preformed iodinin 1/α-CD 1 complexes overloaded with an additional amount of iodinin in the THF phase. The total concentration of iodinin was $1.6 \cdot 10^{-4}$ M (iodinin/CD=2). The relevant solution of the preformed complex in THF (25 mL) was poured dropwise into deionized water (50 mL) with good stirring. A slightly turbid emulsion of nanospheres formed spontaneously. Solvent and a part of water were evaporated under reduced pressure and the total volume adjusted to 50 mL.

b) Nanoparticles Analysis

The mean particle size (diameter, nm) and the polydispersity index (PdI) of nanospheres were measured by dynamic light scattering using a NanoZS instrument, which analyses the fluctuations of scattered light intensity generated by diffusion of the particles in diluted suspension. The measurements were carried out at 25° C. Each value is the average of three measurements. The encapsulation efficiency was expressed in terms of associated drug percentage:

$$\text{Associated drug (\%)} = \frac{\text{[determined iodinin quantity (mol)]}}{\text{[initial iodinin quantity (mol)]}} \times 100$$

Results are reported in table 1:

TABLE 1

Characteristics of loaded nanoparticles made from amphiphilic α-cyclodextrins.

| Derivative | Nanoparticle size (nm) | PdI | Associated drug (%) |
|---|---|---|---|
| α-$C_4H_9$ | 156 | 0.348 | 44 |
| α-$C_4F_9$ | 109 | 0.352 | 26 |
| α-$C_6H_{13}$ | Error | — | 54 |
| α-$C_6F_{13}$ | 97 | 0.282 | 78 |
| α-$C_8H_{17}$ | 104 | 0.298 | 55 |

b) Nanoparticles Biological Testing In Vitro

IPC-81 Leukaemia cells were incubated for 48 h with 10 or 3% of the formulations (either empty or iodinin-filled cyclodextrin). Apoptosis was assessed by microscopic evaluation. The results (data presented as % apoptotic cells) are shown in the FIGURE.

EXAMPLE 4

Synthesis of Iodinin

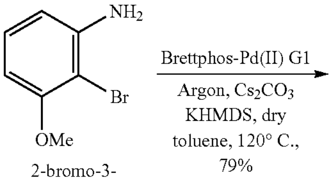

2-bromo-3-methoxyaniline
CAS 112970-44-2
Commercially available in bulk

-continued

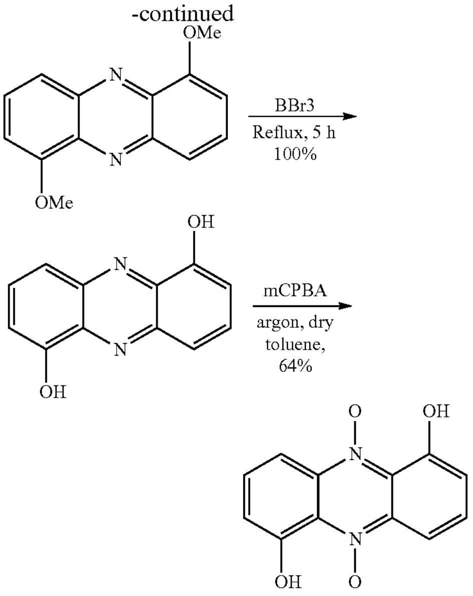

Iodinin a) Synthesis of 1, 6-dimethoxyphenazine

To a dry, and argon filled flask were added 2-Br-3-methoxyaniline (490 mg, 2.43 mmol), BrettPhos Pd G1 catalyst (Sigma Aldrich, 40 mg, 0.05 mmol), KHMDS (10 mg, 0.05 mmol), and $Cs_2CO_3$ (1.66 g, 4.86 mmol). Dry and degassed toluene (8 mL) was added to the inert system, and the reaction was carried out under reflux (120° C.) for 24 h. The reaction mixture was then diluted with chloroform and filtered over a plug of celite and silica, followed by column chromatography on silica gel eluted with a gradient of EtOAc (10-30%) in DCM. Fractions containing product were collected and dried in vacuo to give 1,6-dimethoxyphenazine (204 mg, 0.35 mmol, 79% yield) as a yellow crystalline product: $R_f$=0.51 (100% EtOAc).

$^1$H-NMR: δ (400 MHz, Chloroform-d) 7.96 (d, J=8.9 Hz, 2H), 7.70 (t, J=8.2 Hz, 2H), 7.06 (d, J=7.6 Hz, 2H), 4.14 (s, 6H).

$^{13}$C-NMR: δ (101 MHz, Chloroform-d) 154.89, 142.99, 136.86, 130.06, 122.02, 106.81, 56.43.

b) Synthesis of 1,6-dihydroxyphenazine

The preparation of this compound was achieved using the route described by Alonso et al., 2005. Boron tribromide (5 g, 20 mmol) was added to 1,6-dimethoxyphenazine (230 mg, 096 mmol) under Argon. The mixture was refluxed for 5 h, then cooled to room temperature. The reaction mixture was the cooled to −25° C. and quenched by dropping ice water to the solution. The pH of the solution was adjusted to 7 using 0.1M NaOH. The yellow precipitate was filtered off, and washed with water and cold acetone. Product was dried in vacuo to give 1,6-dihydroxyphenazine (203 mg, 100% yield) as a yellow crystalline product: $R_f$=0.42 (100% EtOAc).

$^1$H-NMR: δ (600 MHz, DCM-d2) 8.20 (s, 2H), 7.82-7.77 (m, 4H), 7.26 (dd, J=5.7, 2.8 Hz, 2H).

$^{13}$C-NMR: δ (151 MHz, DCM-d2) 152.42, 142.13, 135.98, 132.39, 119.92, 109.72.

c) Synthesis of 1,6-dihydroxyphenazine-5N,10N-dioxide (iodinin)

m-CPBA (125 mg, 5 eq, Sigma Aldrich 77% max) was added to a solution of 1,6-dihydroxyphenazine (30 mg, 0.14 mmol) in toluene (7 mL). The reaction mixture was shielded from light and stirred under Argon for 7 h at 70° C. 150 mg of m-CPBA was added every second hour. When completed, the reaction mixture was diluted with DCM and filtered over celite, followed by column chromatography on silica gel eluted with 100% DCM. Fractions with products were combined and solvent was removed with rotary evaporation. Impurities were removed by washing the dried product with cold $Et_2O$, which gave Iodinin (26 mg, 64%) as a purple/copperish crystalline product: $R_f$=0.95 (100% EtOAc).

$^1$H-NMR: δ ($CDCl_3$) 14.05 (s, 2H), 8.00 (dd, J=9.1, 1.1 Hz, 2H), 7.69 (dd, J=9.0, 7.9 Hz, 2H), 7.13 (dd, J=7.9, 1.1 Hz, 1H).

$^{13}$C-NMR: δ (151 MHz, DMSO-$d_6$) 152.48, 134.99, 133.41, 126.66, 113.97, 107.42.

EXAMPLE 5

General Procedure for Mono- or Di-Alkylation of Iodinin and Alkylation of Myxin (Used in Example 6)

Iodinin from Example 4c (1 mmol), $K_2CO_3$ (1-10 mmol) and 18-crown-6-ether (1-2 mmol) were dispersed in anhydrous DMF (10 mL). The resulting mixture was cooled down to 0° C. and alkylating agent (1.25 eq for monoalkylation of iodinin or myxin, 2.5 equivalents for dialkylation of iodinin) added and the reaction mixture left stirring overnight gradually reaching ambient temperature. The reaction mixture was diluted by $H_2O$ (250 mL) and extracted with EtOAc (4×50 mL). The organic phases were pooled and washed with brine (4×100 mL) and dried over $MgSO_4$ and filtered before solvents were removed under reduced pressure. The resulting crude compound was dry loaded on silica and further purified by flash column chromatography on silica (10-50% EtOAc as the eluent) to yield mono- or dialkylated iodinin or alkylated myxin.

EXAMPLE 6

Synthesis of Myxin

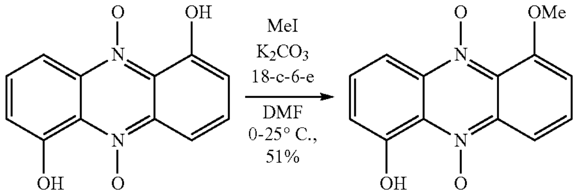

1,6-dihydroxy-phenazine-5N-, 10N-dioxide (iodinin).

1-hydroxy-6-methoxy phenazine-5N-, 10N-dioxide (myxin).

A dry round bottomed flask was charged with iodinin from Example 4c (71 mg, 0.29 mmol), $K_2CO_3$ (40.1 mg, 0.29 mmol) and 18-crown-6-ether (76.6 mg, 0.29 mmol) and dispersed in anhydrous DMF (4 mL). The resulting mixture was cooled down to 0° C. and MeI (0.02 mL, 0.36 mmol, 1.25 eq) added and the reaction mixture left stirring overnight gradually reaching ambient temperature. The reaction mixture was diluted by $H_2O$ (200 mL) and extracted with EtOAc (4×25 mL). The organic phases were pooled and washed with brine (4×100 mL), dried over $MgSO_4$ and filtered before solvents were removed under reduced pressure. The resulting crude compound was dry loaded on silica and further purified by flash column chromatography on silica (10-50% EtOAc as the eluent) affording 38 mg (51%) of Myxin as a bright red solid. $R_f$: 0.59 (100% EtOAc).

$^1H$ NMR (600 MHz, Chloroform-d) δ 14.57 (s, 1H), 8.21 (dd, J=9.0, 1.1 Hz, 1H), 8.01 (dd, J=9.0, 1.1 Hz, 1H), 7.64 (ddd, J=25.0, 9.0, 7.9 Hz, 2H), 7.11 (dd, J=7.9, 1.1 Hz, 1H), 7.08-7.05 (m, 1H), 4.08 (s, 3H).

$^{13}C$ NMR (151 MHz, $CDCl_3$) δ 153.9, 153.8, 138.8, 136.0, 132.5, 131.8, 130.0, 125.9, 115.0, 110.7, 109.8, 107.0, 57.4.

$^1H$ and $^{13}C$ NMR data are in accordance with literature (Chowdhury et al, *Chemical Research in Toxicology* 2011, 25 (1), 197-206).

All reagents 7a-7f, 7h and propargyl-bromide are reacted with iodinin or myxin as described in Example 5 to yield the respective acetonide protected product.

Scheme 11 Commercial reagents for use in the invention, as depicted for myxin in Example 7

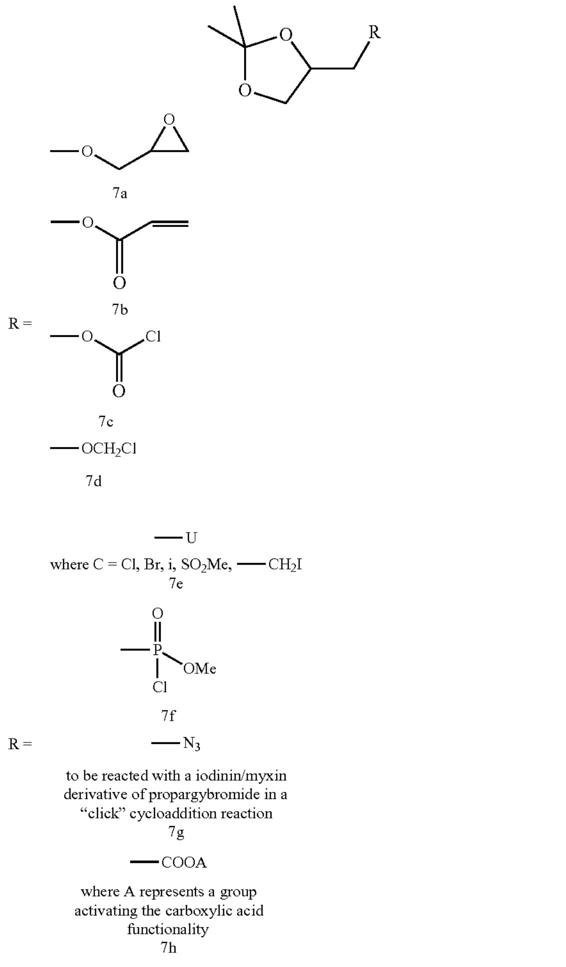

7a) 3-(2-hydroxy-3-(6-methoxyphenazin-1-yl)oxy) propoxy)propane-1,2-diol-N,N-dioxide

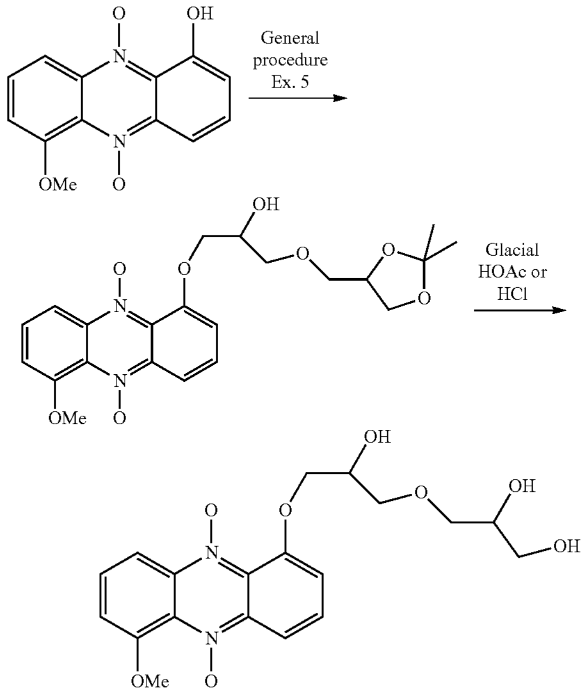

Myxin from Example 6 was alkylated following the general procedure in Example 5. The acetonide was cleaved as described in Lewbart et al, J. Org. Chem. 34 (1969) 3505. The resulting solution was evaporated to dryness. The resulting crude compound was dry loaded on silica and further purified by flash column chromatography on silica (10-50% $H_2O$/EtOAc as the eluent) affording a red solid.

EXAMPLE 8

Synthesis of the Ammonium Salt of the Bis Phosphoric Acid Ester of Iodinin

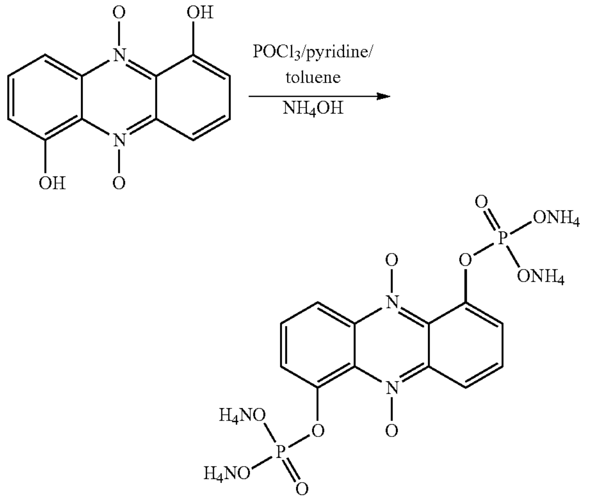

The compound was prepared using a modified procedure described by Huffman, John W. et al. in Bioorganic & Medicinal Chemistry, 11(7), 1397-1410; 2003. To a stirred solution of iodinin (1 mmol, 1.0 equiv) and phosphorus oxychloride (2.75 mL, 30.0 mmol, 30.0 equiv) in toluene (20 mL) cooled to 0° C. was added dropwise a solution of pyridine (191 μL, 2 mmol, 2.0 equiv) in toluene (10 mL). The mixture was stirred for 5 h at 0° C. Subsequently ether (75 mL) was added. The remaining solids were removed, and the solvent was evaporated. The excess of phosphorus oxychloride was removed under vacuum. Ammonium hydroxide solution (28%) was added dropwise to the residue at 0° C. until pH 7 was attained. The solvent was evaporated, and a violet solid was obtained. The crude product was redissolved in methanol:water (1:1) and purified on a silica flash column using a stepwise gradient, starting with water, followed by acetonitrile: water going from 50% to 80% acetonitrile. The solvent was evaporated under reduced pressure. The title compound was obtained as a red-violet solid. The ammonium salt of the phosphoric acid ester of myxin was prepared analogously.

EXAMPLE 9

PEGylations of Iodinin and Myxin with Triethylene Glycol Derivatives

9a—Synthesis of Triethylene Glycol (TEG) Reagents

TEG Monomethyl Ether Tosylate

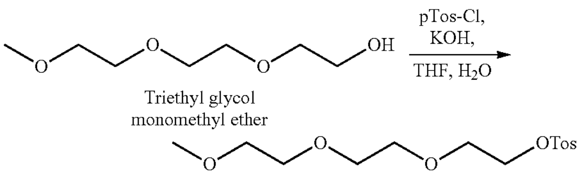

Triethyl glycol monomethyl ether

TEG-monomethyl ether tosylate

Triethylene glycol monomethyl ether (5.0 mL, 31.2 mmol) is dissolved in THF (30 mL) stirring at room temperature. A solution of KOH (3.68 g, 65.6 mmol) in 25 mL of $H_2O$ is slowly added and the resulting mixture cooled down to 0° C. To this, para-toluene sulfonyl chloride (9.53 g, 50 mmol) dissolved in THF (50 mL) is added dropwise over a period of 30 min. The resulting mixture is stirred overnight gradually allowed to reach ambient temperature. The mixture is concentrated under reduced pressure to remove THF and diluted by 40 mL of EtOAc and 60 mL of $H_2O$. Organic layer is separated and the aqueous phase extracted by 3×30 mL portions of EtOAc. Combined organic phases are washed with brine (2*100 mL), dried over $M_gSO_4$, filtered and concentrated in vacuo affording TEG monomethyl ether tosylate as a clear oily material. If necessary, flash column chromatography is used for further purification.

TEG Monoethyl Ether Tosylate

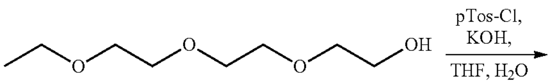

Triethyl glycol monomethyl ether

-continued

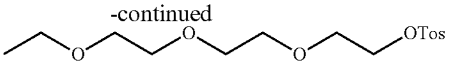

TEG-monomethyl ether tosylate

Triethylene glycol monoethyl ether (5.0 mL, 28.61) is dissolved in THF (30 mL) stirring at room temperature. A solution of KOH (3.69 g, 65.8 mmol) in 25 mL of $H_2O$ is slowly added and the resulting mixture cooled down to 0° C. To this, para-toluene sulfonyl chloride (9.49 g, 49.8 mmol) dissolved in THF (50 mL) is added dropwise over a period of 30 min. The resulting mixture is stirred overnight gradually allowed to reach ambient temperature. The mixture is concentrated under reduced pressure to remove THF and diluted by 40 mL of EtOAc and 60 mL of $H_2O$. Organic layer is separated and the aqueous phase extracted by 3×30 mL portions of EtOAc. Combined organic phases are washed with brine (2*100 mL), dried over $M_gSO_4$, filtered and concentrated in vacuo affording TEG monomethyl ether tosylate as a clear oily material. If necessary, flash column chromatography is used for further purification.

9b—PEGylations of Myxin with Triethylene Glycol Derivatives

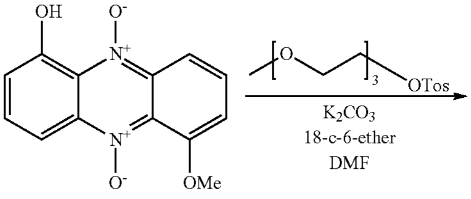

Myxin

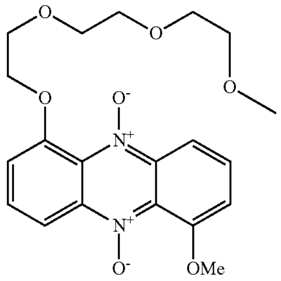

TEG-monomethyl ether (1.2 equiv.) is added to a stirring solution of Myxin (1 equiv.), $K_2CO_3$ (1 equiv.) and 18-crown-6-ether (1 equiv.) in anhydrous DMF under an argon atmosphere at 0° C. Resulting mixture is left stirring overnight gradually reaching ambient temperature before it is concentrated under reduced pressure. The resulting crude is diluted by $H_2O$ and the aqueous phase extracted 3 times with EtOAc. Organic phases are combined and washed with brine and dried over $MgSO_4$. Solvents are removed under reduced pressure and the resulting crude product further purified by flash column chromatography if necessary (based on TLC and crude $^1H$ NMR).

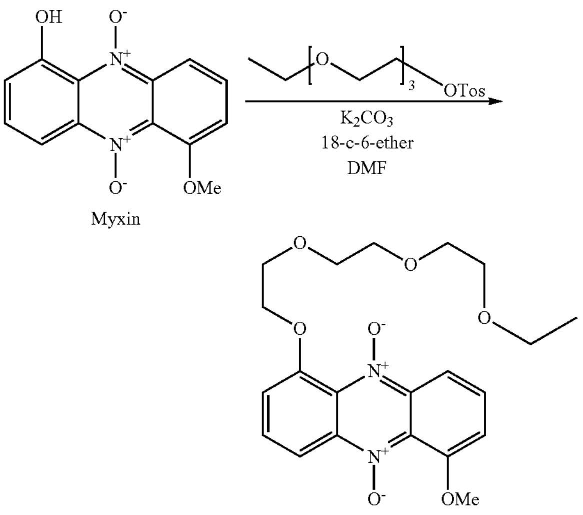

Myxin

TEG-monoethyl ether (1.2 equiv.) is added to a stirring solution of Myxin (1 equiv.), $K_2CO_3$ (1 equiv.) and 18-crown-6-ether (1 equiv.) in anhydrous DMF under an argon atmosphere at 0° C. Resulting mixture is left stirring overnight gradually reaching ambient temperature before it is concentrated under reduced pressure. The resulting crude is diluted by $H_2O$ and the aqueous phase extracted 3 times with EtOAc. Organic phases are combined and washed with brine and dried over $MgSO_4$. Solvents are removed under reduced pressure and the resulting crude product further purified by flash column chromatography if necessary (based on TLC and crude $^1H$ NMR).

9c—Single Tegylated Iodinin

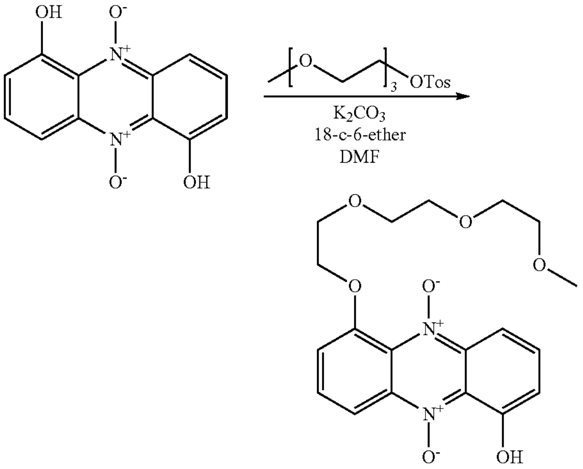

TEG-monomethyl ether (1.2 equiv.) is added to a stirring solution of iodinin (1 equiv.), $K_2CO_3$ (1 equiv.) and 18-crown-6-ether (1 equiv.) in anhydrous DMF under an argon atmosphere at 0° C. Resulting mixture is left stirring overnight gradually reaching ambient temperature before it is concentrated under reduced pressure. The resulting crude is diluted by $H_2O$ and pH adjusted to 7 by dilute HCl if necessary. The aqueous phase is extracted 3 times with EtOAc. Organic phases are combined and washed with brine and dried over $MgSO_4$. Solvents are removed under reduced pressure and the resulting crude product further purified by flash column chromatography if necessary (based on TLC and crude $^1H$ NMR).

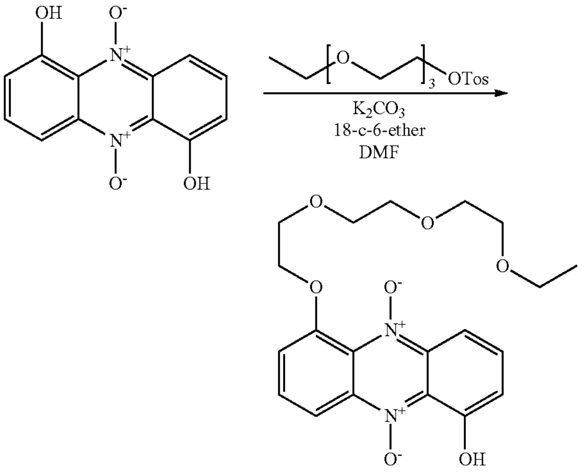

TEG-monoethyl ether (1.2 equiv.) is added to a stirring solution of iodinin (1 equiv.), $K_2CO_3$ (1 equiv.) and 18-crown-6-ether (1 equiv.) in anhydrous DMF under an argon atmosphere at 0° C. Resulting mixture is left stirring overnight gradually reaching ambient temperature before it is concentrated under reduced pressure. The resulting crude is diluted by $H_2O$ and pH adjusted to 7 by dilute HCl if necessary. The aqueous phase is extracted 3 times with EtOAc. Organic phases are combined and washed with brine and dried over $MgSO_4$. Solvents are removed under reduced pressure and the resulting crude product further purified by flash column chromatography if necessary (based on TLC and crude $^1H$ NMR).

9d—Di-TEGylated Iodnin Derivatives

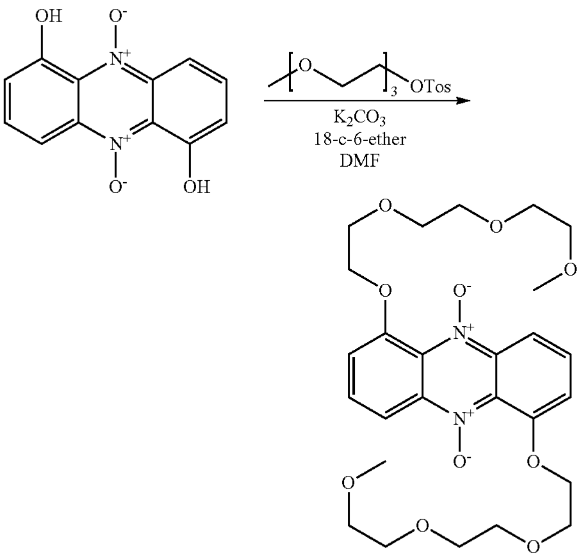

TEG-monomethyl ether (2.5 equiv.) is added to a stirring solution of iodinin (1 equiv.), $K_2CO_3$ (2 equiv.) and 18-crown-6-ether (2 equiv.) in anhydrous DMF under an argon atmosphere at 0° C. Resulting mixture is left stirring overnight gradually reaching ambient temperature before it is concentrated under reduced pressure. The resulting crude is diluted by $H_2O$. The aqueous phase is extracted 4 times with EtOAc. Organic phases are combined and washed with brine and dried over $MgSO_4$. Solvents are removed under reduced pressure and the resulting crude product further purified by flash column chromatography if necessary.

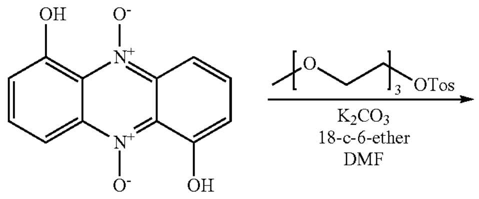

-continued

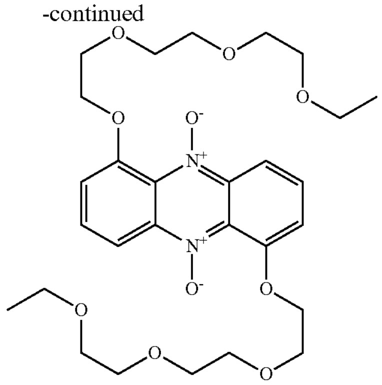

TEG-monoethyl ether (2.5 equiv.) is added to a stirring solution of iodinin (1 equiv.), $K_2CO_3$ (2 equiv.) and 18-crown-6-ether (2 equiv.) in anhydrous DMF under an argon atmosphere at 0° C. Resulting mixture is left stirring overnight gradually reaching ambient temperature before it is concentrated under reduced pressure. The resulting crude is diluted by $H_2O$. The aqueous phase is extracted 4 times with EtOAc. Organic phases are combined and washed with brine and dried over $MgSO_4$. Solvents are removed under reduced pressure and the resulting crude product further purified by flash column chromatography if necessary.

EXAMPLE 10

Synthesis of iodinin-1,6-diamino-1,6-dideoxy-hexitol block-copolymer

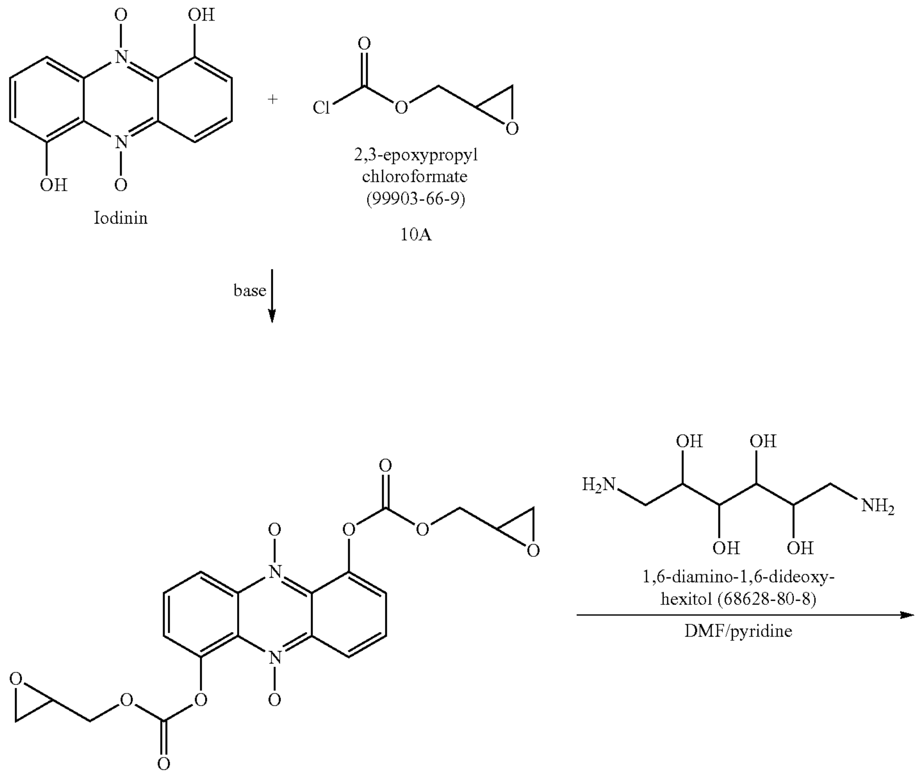

Iodinin 2,3-epoxypropyl chloroformate (99903-66-9)

10A 1,6-diamino-1,6-dideoxy-hexitol (68628-80-8)

10B

-continued

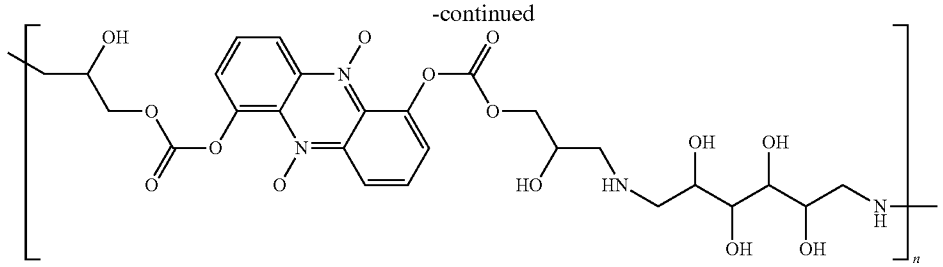

10C

The bis-epoxide 10B is prepared mixing iodinin, 3 equivalents of the commercially available 2,3-epoxypropyl chloroformate (99903-66-9) and 3 equivalents of pyridine in DMF (1:10 weight iodinin/weight DMF). The resulting solution is mixed with dichloromethane (2× the volume of DMF), the resulting solution is washed 3 times with brine, and three times with 10% acetic acid in water. A copolymer of iodinin and commercially available 1,6-diamino-1,6-dideoxy-hexitol (68628-80-8) is prepared as described in U.S. Pat. No. 4,072,633. The dichloromethane solution containing 10B solution is added tp 3 equivalents of commercially available 1,6-diamino-1,6-dideoxy-hexitol (68628-80-8) in a volume of DMF equal to the volume of dichloromethane. The solution is stirred for an ambient time, evaporated, and the resulting solid is fractionated using size exclusion chromatography.

EXAMPLE 11

Synthesis of Glycidol Derived Analogs of Iodinin and Myxin

11a—Synthesis of 1-(1,2-dihydroxyethoxy)-6-(2,3-dihydroxypropoxy)phenazine 5,10-dioxide

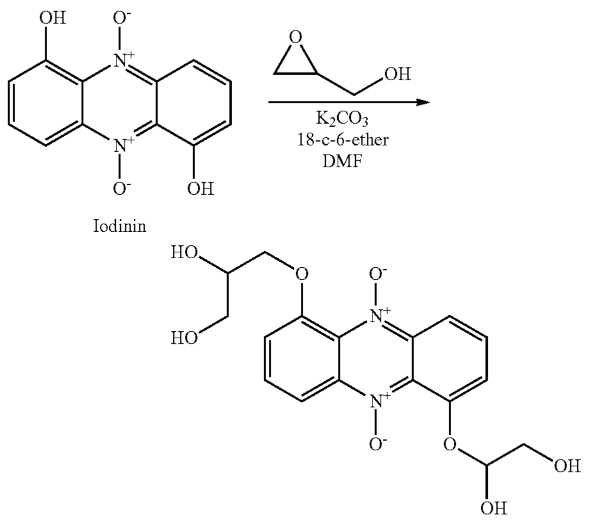

Iodinin 1-(1,2-dihydroxyethoxy)-6-(2,3-dihydroxypropoxy)phenazine 5,10-dioxide

Glycidol (2.5 equiv.) is added to a stirring solution of iodinin (1 equiv.), $K_2CO_3$ (2 equiv.) and 18-crown-6-ether (2 equiv.) in anhydrous DMF under an argon atmosphere at 0° C. The resulting mixture is left stirring overnight gradually reaching ambient temperature before it is concentrated under reduced pressure. The resulting crude is diluted by $H_2O$. The aqueous phase is extracted 4 times with EtOAc. Organic phases are combined and washed with brine and dried over $MgSO_4$. Solvents are removed under reduced pressure and the resulting crude product further purified by flash column chromatography if necessary.

11b—Synthesis of 1-(1,2-dihydroxyethoxy)-6-hydroxyphenazine 5,10-dioxide

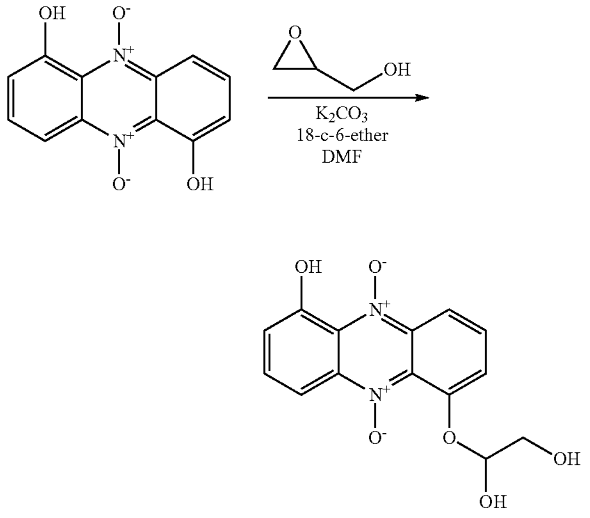

1-(1,2-dihydroxyethoxy)-6-hydroxyphenazine 5,10-dioxide

Glycidol (1.2 equiv.) is added to a stirring solution of iodinin (1 equiv.), $K_2CO_3$ (2 equiv.) and 18-crown-6-ether (2 equiv.) in anhydrous DMF under an argon atmosphere at 0° C. The resulting mixture is left stirring overnight gradually reaching ambient temperature before it is concentrated under reduced pressure. The resulting crude is diluted by $H_2O$ and pH adjusted to 7 by dilute HCl if necessary. The aqueous phase is extracted 4 times with EtOAc. Organic phases are combined and washed with brine and dried over $MgSO_4$. Solvents are removed under reduced pressure and the resulting crude product further purified by flash column chromatography if necessary.

11c—Synthesis of 1-(2,3-dihydroxypropoxy)-6-methoxyphenazine 5,10-dioxide

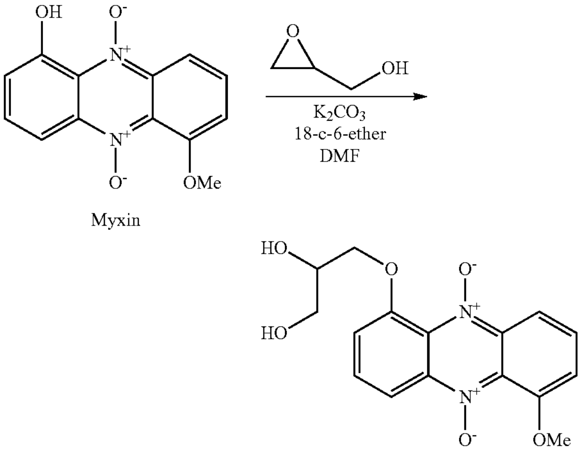

Myxin 1-(2,3-dihydroxypropoxy)-6-methoxyphenazine 5,10-dioxide

Glycidol (1.2 equiv.) is added to a stirring solution of Myxin (1 equiv.), $K_2CO_3$ (2 equiv.) and 18-crown-6-ether (2 equiv.) in anhydrous DMF under an argon atmosphere at 0° C. The resulting mixture is left stirring overnight gradually reaching ambient temperature before it is concentrated under reduced pressure. The resulting crude is diluted by $H_2O$. The aqueous phase is extracted 4 times with EtOAc. Organic phases are combined and washed with brine and dried over $MgSO_4$. Solvents are removed under reduced pressure and the resulting crude product further purified by flash column chromatography if necessary.

EXAMPLE 12

Synthesis of Precursors for Myxin and Iodinin Biodegradable Prodrugs

12a—Synthesis of 1-(2-chloroacetoxy)-6-methoxyphenazine 5,10-dioxide

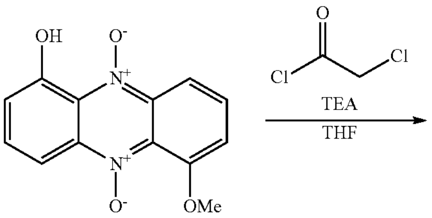

Myxin

-continued

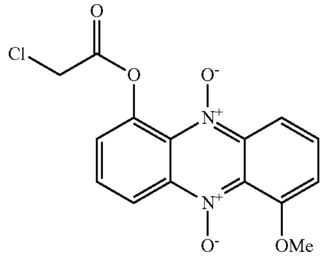

1-(2-chloroacetoxy)-6-methoxyphenazine 5,10-dioxide

Chloroacetylchloride (1 equiv.) is added drop-wise to a stirring solution of Myxin (1 equiv.) and TEA (1.1 equiv.) in anhydrous THF at 0° C. The mixture is left stirring for 30 min and gradually allowed to reach ambient temperature and left stirring for an additional period of 3 hours. The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

12b—Synthesis of 1-(2-chloroacetoxy)-6-hydroxyphenazine 5,10-dioxide

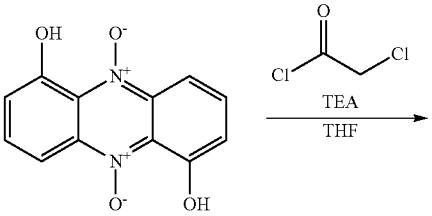

Iodinin

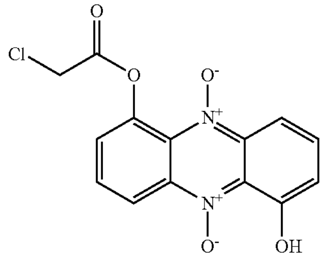

1-(2-chloroacetoxy)-6-methoxyphenazine 5,10-dioxide

Chloroacetylchloride (1.2 equiv.) is added drop-wise to a stirring solution of iodinin (1 equiv.) and TEA (1.1 equiv.) in anhydrous THF at 0° C. The mixture is left stirring for 30 min and gradually allowed to reach ambient temperature and left stirring for an additional period of 3 hrs. The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

12c—Synthesis of 1,6-bis(2-chloroacetoxy)phenazine 5,10-dioxide

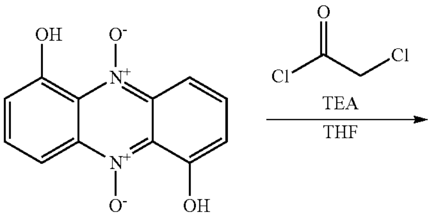

Iodinin

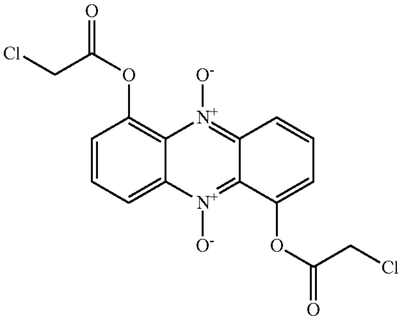

1,6-bis(2-chloroacetoxy)phenazine 5,10-dioxide

Chloroacetylchloride (1.2 equiv.) is added drop-wise to a stirring solution of iodinin (1 equiv.) and TEA (1.1 equiv.) in anhydrous THF at 0° C. The mixture is left stirring for 30 min and gradually allowed to reach ambient temperature and left stirring for an additional period of 3 hrs. The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

12d—Synthesis of 1-(2-((2,2-dimethyl-1,3-dioxolan-4-yl)methoxy)acetoxy)-6-hydroxyphenazine 5,10-dioxide

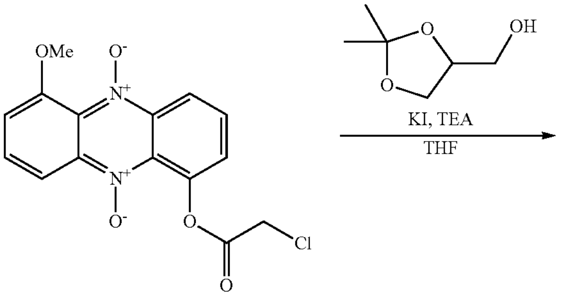

1-(2-chloroacetoxy)-6-methoxyphenazine 5,10-dioxide

-continued

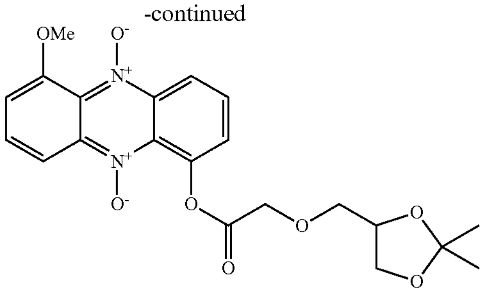

1-(2-((2,2-dimethyl-1,3-dioxolan-4-yl)methoxy)acetoxy)-6-methoxyphenazine 5,10-dioxide DL-1,2-Isopropylideneglycerol (1.2 equiv.) is added drop-wise to a stirring solution of 1-(2-chloroacetoxy)-6-methoxyphenazine 5,10-dioxide (1 eq.), KI (1.2 equiv.) and TEA (1.1 equiv.) in anhydrous THF under an argon atmosphere at 0° C. The mixture is left stirring for 30 min and gradually allowed to reach ambient temperature and left stirring for an additional period until completion (2-48 hrs estimated by TLC). The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

12e—Synthesis of 1-(2-((2,2-dimethyl-1,3-dioxolan-4-yl)methoxy)acetoxy)-6-hydroxyphenazine 5,10-dioxide

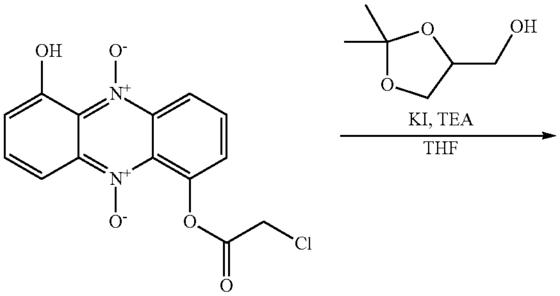

1-(2-chloroacetoxy)-6-hydroxyphenazine 5,10-dioxide

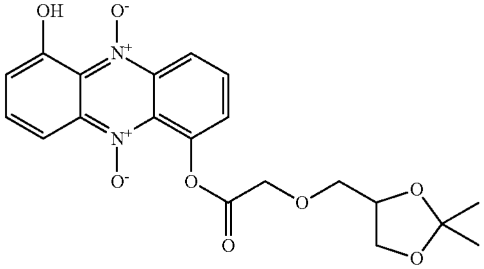

1-(2-((2,2-dimethyl-1,3-dioxolan-4-yl)methoxy)acetoxy)-6-hydroxyphenazine 5,10-dioxide DL-1,2-Isopropylideneglycerol (1.2 equiv.) is added drop-wise to a stirring solution of 1-(2-chloroacetoxy)-6-hydroxyphenazine 5,10-dioxide (1 eq.), KI (1.2 equiv.) and TEA (1.1 equiv.) in anhydrous THF under an argon atmosphere at 0° C. The mixture is left stirring for 30 min and gradually allowed to reach ambient temperature and left stirring for an additional period until completion (2-48 hrs estimated by TLC). The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

12f—Synthesis of 1,6-bis(2-((2,2-dimethyl-1,3-dioxolan-4-yl)methoxy) acetoxy)phenazine 5,10-dioxide

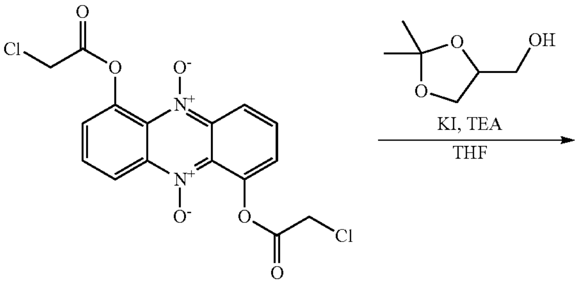

1,6-bis(2-chloroacetoxy) phenazine 5,10-dioxide

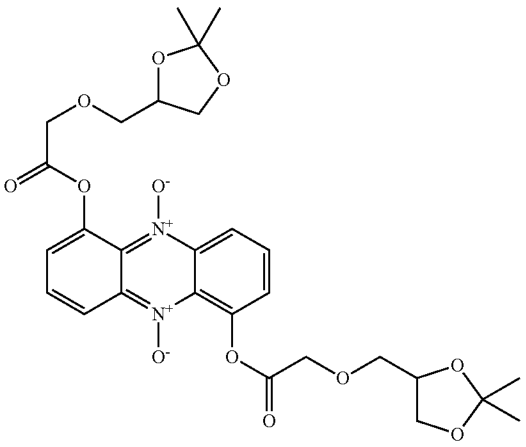

1,6-bis(2-((2,2-dimethyl-1,3-dioxolan-4-yl) methoxy)acetoxy)phenazine 5,10-dioxide DL-1,2-Isopropylideneglycerol (2.5 equiv.) is added drop-wise to a stirring solution of 1,6-bis(2-chloroacetoxy) phenazine 5,10-dioxide (1 eq.), KI (2.4 equiv.) and TEA (2.2 equiv.) in anhydrous THF under an argon atmosphere at 0° C. The mixture is left stirring for 30 min and gradually allowed to reach ambient temperature and left stirring for an additional period until completion (2-48 hrs estimated by TLC). The crude mixture is concentrated in vacuo, then diluted by $H_2O$ and extracted by 4 portions of EtOAc. Combined organic phases are pooled and dried over $MgSO_4$, filtered and concentrated. The resulting crude compound is purified by flash column chromatography if necessary.

EXAMPLE 13

General Experimental Procedure for Deprotection of Dimethylacetals

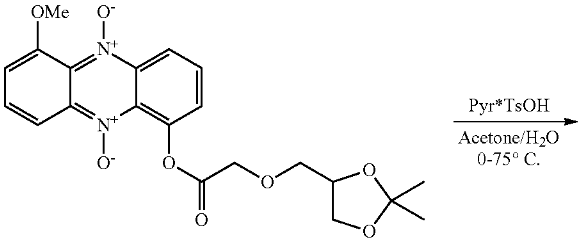

1-(2-((2,2-dimethyl-1,3-dioxolan-4-yl)methoxy)acetoxy)-6-methoxyphenazine 5,10-dioxide

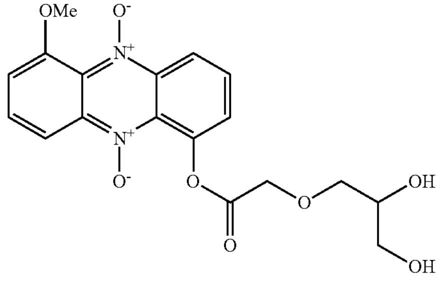

1-(2-(2,3-dihydroxypropoxy)acetoxy)-6-methoxyphenazine 5,10-dioxide 1-(2-((2,2-dimethyl-1,3-dioxolan-4-yl)methoxy)acetoxy)-6-methoxyphenazine 5,10-dioxide is dissolved in $H_2O$/acetone solvent combination and cooled down to 0° C. before pyridinium p-toluenesulfonate (PPTS) is added. The reaction mixture is stirred until complete consumption of the starting material is observed by TLC (warmed up to 75° C. if necessary). The crude mixture is then concentrated under reduced pressure and further purified by recrystallization from an appropriate solvent mixture or by flash column chromatography if necessary.

The invention claimed is:

1. A compound of formula I, or a physiologically acceptable salt thereof:

(I)

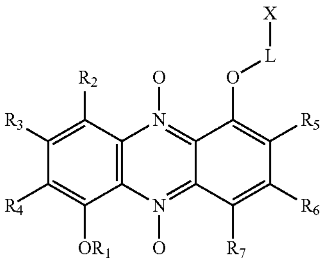

wherein $R_1$ is selected from:

hydrogen, methyl, and a group -L-X in which L and X are as defined herein;

$R_2$, $R_3$, $R_4$, $R_5$, $R_6$, and $R_7$ are each hydrogen;

L is either a direct bond or a linker;

X is a functional group selected from:

$-PO_2OH$

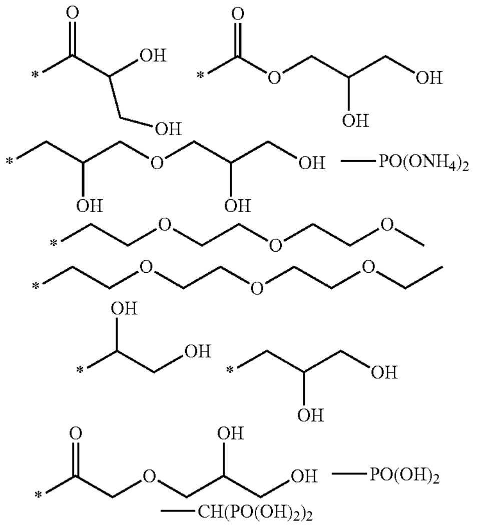

$-PO(ONH_4)_2$ $-PO(OH)_2$ $-CH(PO(OH)_2)_2$ wherein * denotes the point of attachment to L, where present, or directly to the O atom, or X is a functional group selected from lactic acid, lactide and a vinylic group, or X is a biocompatible polymer selected from polylysine, dextran, polylactic acid, chitosan and alginate; and wherein, when $R_1$ is a group -L-X, each L and X may be the same or different.

2. A compound as claimed in claim 1, wherein L is a linker which is a $C_{1-8}$ alkylene group optionally substituted by one or more groups selected from $C_{1-3}$ alkyl, hydroxy, $C_{1-6}$ alkoxy, wherein one or more methylene groups within the backbone of the linker may each additionally be replaced by a group selected from —O—, —S—, —NH—, —NR— wherein R is $C_{1-3}$ alkyl, and —CO—, and wherein two adjacent methylene groups within the backbone of the linker may each additionally carry substituents which, together with the intervening atoms of the linker backbone, form an optionally substituted, 5- or 6-membered saturated ring.

3. A compound as claimed in claim 1, wherein L is a linker which includes one or more groups selected from —C(O)O—, —OC(O)—NR—, —OC(O)—O—, —C(O)—NR—, and —CO— wherein R is hydrogen or $C_{1-3}$ alkyl.

4. A compound as claimed in claim 1, wherein L represents the following group:

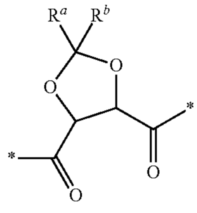

where $R^a$ and $R^b$ are independently selected from hydrogen and $C_{1-3}$ alkyl; and

* denotes the point of attachment of the linker to adjacent groups within the molecule.

5. A compound as claimed in claim 1, wherein X is acrylic acid.

6. A compound as claimed in claim 1, wherein X is polylysine.

7. A compound as claimed in claim 1, which is provided in the form of a physiologically acceptable salt.

8. A compound as claimed in claim 7, wherein the salt is selected from $Na^+$, $K^+$, $Ca^+$, $Mg_+$, or hydrophilic ammonium salts with methyl-glucamine, glucosamine, chitosan or alginate.

9. A compound as claimed in claim 1, which is provided in the form of a complex with at least one chelating agent.

10. A compound as claimed in claim 9, wherein said agent is an inclusion agent.

11. A compound as claimed in claim 10, wherein the inclusion agent is selected from the group consisting of cyclodextrins and calixarenes.

12. A compound as claimed in claim 9 provided in the form of nanoparticles.

13. A compound as claimed in claim 1, which is provided in the form of nanoparticles comprising micelles or liposomes formed from one or more surface active agents.

14. A compound as claimed in claim 13, wherein the surface active agents are selected from triglycerides, soaps and other carboxylates, anionic surfactants, proteins, sulfates sulfonates, ethoxylated alcohols and alkylphenols, fatty acid esters, nitrogenated nonionic surfactants, linear alkyl-amines, alkyl-ammoniums, nitrogenated surfactants with a second hydrophile, amphoteric surfactants, silicon surfactants, fluorinated surfactants, polymeric surfactants or surfactant polymers or association polymers.

15. A compound which is a polymer having the formula:

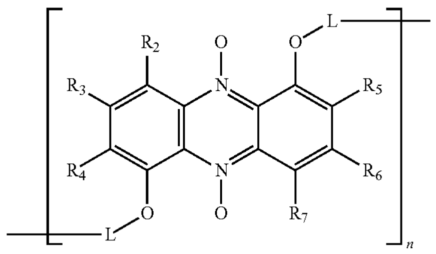

wherein n is an integer of at least 2;

each of $R_2$, $R_3$, $R_4$, $R_5$, $R_6$ and $R_7$ is hydrogen; and

L is either a direct bond or a linker.

16. A compound as claimed in claim 15, wherein L is selected from the following structures:

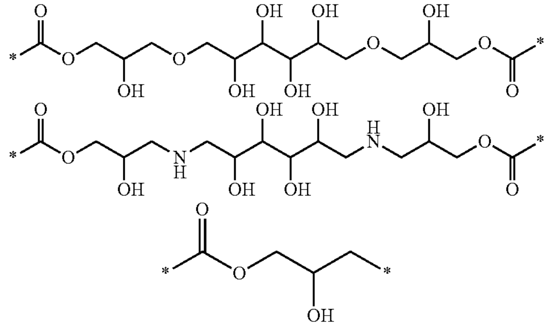

-continued
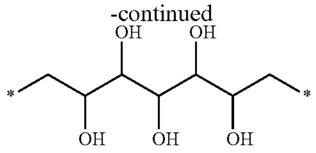
wherein each * denotes the point of attachment of the linker, L, to adjacent groups within the molecule.
17. A pharmaceutical composition comprising a compound as claimed in claim 1 or a physiologically acceptable salt thereof, together with one or more pharmaceutically acceptable carriers or excipients.
* * * * *